US010613084B2

(12) United States Patent
Middelveen et al.

(10) Patent No.: US 10,613,084 B2
(45) Date of Patent: Apr. 7, 2020

(54) METHOD OF CULTURING BORRELIA SPIROCHETES AND OF DIAGNOSING BORRELIA INFECTIONS, AND A DIAGNOSTIC KIT FOR USE IN THE METHODS

(71) Applicants: Marianne Middelveen, Calgary (CA); Raphael Stricker, San Francisco, CA (US)

(72) Inventors: Marianne Middelveen, Calgary (CA); Raphael Stricker, San Francisco, CA (US)

( * ) Notice: Subject to any disclaimer, the term of this patent is extended or adjusted under 35 U.S.C. 154(b) by 154 days.

(21) Appl. No.: 15/539,442

(22) PCT Filed: Dec. 23, 2015

(86) PCT No.: PCT/US2015/000204
§ 371 (c)(1),
(2) Date: Jun. 23, 2017

(87) PCT Pub. No.: WO2016/105479
PCT Pub. Date: Jun. 30, 2016

(65) Prior Publication Data
US 2018/0267038 A1 Sep. 20, 2018

Related U.S. Application Data

(60) Provisional application No. 62/096,136, filed on Dec. 23, 2014.

(51) Int. Cl.
| | | |
|---|---|---|
| *A61K 39/02* | (2006.01) | |
| *A01N 63/00* | (2020.01) | |
| *C12N 1/12* | (2006.01) | |
| *G01N 33/569* | (2006.01) | |
| *C12Q 1/04* | (2006.01) | |
| *C12N 1/20* | (2006.01) | |
| *C12Q 1/686* | (2018.01) | |

(52) U.S. Cl.
CPC ......... *G01N 33/56911* (2013.01); *C12N 1/20* (2013.01); *C12Q 1/04* (2013.01); *C12N 2500/30* (2013.01); *C12Q 1/686* (2013.01); *G01N 2333/20* (2013.01); *G01N 2800/26* (2013.01); *Y02A 50/57* (2018.01)

(58) Field of Classification Search
CPC ............................ A61K 39/00; A61K 39/0225

USPC ................... 424/93.1; 435/243, 252.1, 252.4
See application file for complete search history.

(56) References Cited

U.S. PATENT DOCUMENTS

2001/0036658 A1 11/2001 Phillips et al.
2004/0214316 A1 10/2004 O'Connell

OTHER PUBLICATIONS

Barbour, Alan, G. M.D., "Isolation and Cultivation of Lyme Disease Spirochetes", The Yale Journal of Biology and Medicine, 1984, pp. 521-525, vol. 57, The Yale Journal of Biology and Medicine, Inc.
Pollack, R.J., et al., "Standardization of Medium for Culturing Lyme Disease Spirochetes", Journal of Clinical Microbiology, May 1993, pp. 1251-1255, vol. 31, No. 5, American Society for Microbiology.
Ruzic-Sabljic, Eva, et al., "Comparison of grown of Borrelia afzelii, B. garinii, and B. burgadorferi sensu stricto in MKP and BSK-II medium", International Journal of Medical Microbiology, 2004, pp. 407-412, vol. 294, Elsevier GmbH.
Rodriguez, Islay, et al., "Evaluation of a modified culture medium for Borrelia burgdorferi senso lato", Mem Inst Oswaldo Cruz, Rio de Janeiro, Dec. 2007, pp. 999-1002, vol. 102, No. 8.
Tyagi, Sanjay, et al., "Molecular Beacons in Diagnostics", F1000 Medicine Reports, May 2, 2012, vol. 4, No. 10, 2012 Faculty of 1000 Ltd.
Middelveen, Marianne, J., et al., "Characterization and evolution of dermal filaments from patients with Morgellons disease", Clinical, Cosmetic and Investigational Dermatology, 2013, pp. 1-21, vol. 6, Dove Medical Press Ltd.
Sapi, Eva, et al., "Improved Culture Conditions for the Growth and Detection of Borrelia from Human Serum", Int J Med Sci, 2013, pp. 362-376, vol. 10, No. 4, Ivyspring International Publisher.
Middelveen, Marianne, J., et al., Culture and identification of Borrelia spirochetes in human vaginal and seminal secretions, F1000Research 2014, Dec. 25, 2016, vol. 3, No. 309.
Grier, Tom, "The Difficulty of Culturing Spirochetes", https://www.lymeneteurope.org/info/the-difficulty-of-culturing-spirochetes, downloaded Sep. 20, 2017, LymeNet Europe.

*Primary Examiner* — Rodney P Swartz
(74) *Attorney, Agent, or Firm* — The Webb Law Firm

(57) ABSTRACT

Herein is provided a method that provides a patient, suspected of having Lyme disease, a kit that does not require specialized equipment and allows for easy self-collection of specimens. Methods provided herein, allow for the efficient culturing of *Borrelia* spirochetes, such as *B. burgdorferi* spirochetes after being exposed to an environment that is typically not suitable for *Borrelia* growth.

19 Claims, 3 Drawing Sheets

Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: pyrG outer primer

<400> SEQUENCE: 1
attgcaagtt ctgagaata                                              19

<210> SEQ ID NO 2
<211> LENGTH: 20
<212> TYPE: DNA
<213> ORGANISM: Artificial Sequence
<220> FEATURE:
<223> OTHER INFORMATION: pyrG outer primer

<400> SEQUENCE: 2
caaacattac gagcaaattc                                             20

<210> SEQ ID NO 3
<211> LENGTH: 25
<212> TYPE: DNA
<213> ORGANISM: Artificial Sequence
<220> FEATURE:
<223> OTHER INFORMATION: pyrG inner primer

<400> SEQUENCE: 3
gatatggaaa atattttatt tattg                                       25

<210> SEQ ID NO 4
<211> LENGTH: 20
<212> TYPE: DNA
<213> ORGANISM: Artificial Sequence
<220> FEATURE:
<223> OTHER INFORMATION: pyrG inner primer

<400> SEQUENCE: 4
aaaccaagac aaattccaag                                             20

METHOD OF CULTURING *BORRELIA* SPIROCHETES AND OF DIAGNOSING *BORRELIA* INFECTIONS, AND A DIAGNOSTIC KIT FOR USE IN THE METHODS

CROSS REFERENCE TO RELATED APPLICATIONS

This application is the National Stage of International Patent Application No. PCT/US2015/000204, filed on Dec. 23, 2015, which claims priority to U.S. Provisional Patent Application No. 62/096,136, filed Dec. 23, 2014, each of which is incorporated herein by reference in its entirety.

The Sequence Listing associated with this application is filed in electronic format via EFS-Web and is hereby incorporated by reference into the specification in its entirety. The name of the text file containing the Sequence Listing is 1704569_ST25.txt. The size of the text file is 1,202 bytes, and the text file was created on Apr. 24, 2019.

A method is provided for culturing a *Borrelia* spirochete, e.g. *Borrelia burgdorferi*, and/or identifying an infection thereof in a patient, such as Lyme disease in humans, along with an in-home diagnostic kit and related methods.

Lyme disease is an infectious disease caused by the spirochete *Borrelia burgdorferi*, a tick-borne bacterium infecting animals (e.g., dogs, cats, monkeys, mice and birds) and humans. Lyme disease is transmitted to humans through the bite of an infected blacklegged tick. Typical symptoms include fever, headache, fatigue, arthritis, neurological complications, and a characteristic skin rash called erythema migrans. Because of the difficulty in culturing *Borrelia* bacteria in the laboratory, Lyme disease is initially diagnosed based on symptoms, physical findings (for example, rash), the possibility of exposure to infected ticks, and then subsequently by confirmation through laboratory testing. Upon diagnosis, current drug treatment regimens may include high doses of antibiotics for long durations of time.

The term "spirochete" refers to a phylum of gram-negative bacteria characterized by a long, helical-coil shape. There are several genera of spirochetes, including *Borrelia*, *Treponema*, *Brachyspira* and *Leptospira*. Numerous *Borrelia* genospecies have been identified. Although the *Borrelia burgdorferi* sensu lato group is generally associated with Lyme disease, other *Borrelia* genospecies may cause disease in humans. Examples of *Borrelia* spirochetes that are known to cause disease in humans include *Borrelia afzelii*, *Borrelia bissettii*, *Borrelia burgdorferi* sensu stricto, *Borrelia garinii*, *Borrelia hermsii*, *Borrelia lusitaniae*, *Borrelia miyamotoi*, *Borrelia recurrentis*, *Borrelia spielmanii*, *Borrelia valaisiana* and *Borrelia vincentii*. The full extent of *Borrelia* genospecies that cause disease in humans is unknown at present.

*Borrelia* spirochetes, e.g., *B. burgdorferi* are helically shaped, motile organisms with an outer cell membrane that surrounds a protoplasmic cylinder complex, consisting of the cytoplasm, the cell wall, the inner cell membrane and the flagella which are located not at the cell surface but in the periplasmic space between the outer cell membrane and the protoplasmic cylinder. The outer cell membrane and the flagella are assumed to play an important role in host-parasite interactions during the disease and have been subjected to several investigations, identifying major surface-exposed proteins as important immunogens.

In Lyme disease patients, immunoglobulin M (IgM) antibodies and immunoglobulin G (IgG) antibodies can be detected against proteins including flagellin, OspA, OspB and OspC that are located at the *B. burgdorferi* surface and embedded in its outer fluid cell membrane. Detection of the genes for flagellin, OspA, OspB and OspC protein targets may be used to determine *B. burgdorferi* infection. Other genes in the *B. burgdorferi* genome that are commonly addressed or looked for in the determination of *Borrelia* infection include: 16S rRNA, uvrA, and GAPDH. 16S rRNA is a component of the 30S small subunit of prokaryotic ribosomes. The uvrA gene product in *Borrelia*, is involved in the ability of *B. burgdorferi* to repair intrachain DNA damage. Glyceraldehyde 3-phosphate dehydrogenase (abbreviated as GAPDH) is an enzyme that catalyzes the sixth step of glycolysis and thus serves to break down glucose for energy and carbon molecules. *Borrelia* 16S rRNA, uvrA, and GAPDH genes are unique and distinguishable from both eukaryotic and other prokaryotic forms of the genes, and as such they are reliable markers for the presence of *Borrelia* infection. The *B. burgdorferi* rpoC and pyrG gene targets are also used as indicators of *Borrelia* infection. The rpoC gene encodes for the beta subunit of DNA-directed RNA polymerase, and contains a sequence unique to *Borrelia*. The pyrG gene encodes CTP synthase, which is involved in pyrimidine biosynthesis.

Several forms of laboratory testing for Lyme disease are available, some of which either have not been adequately validated and/or have a history of showing false positives and false negatives. The most widely used tests measure levels of specific antibodies in a patient's blood. These tests may be negative in early infection, as the body may not have produced a sufficient quantity of antibodies. Based on circular reasoning (that is, patients are chosen because they have positive tests, and then tests are found positive), these tests have been considered reliable in the diagnosis of later stages of Lyme disease.

The laboratory tests most widely available and employed are the ELISA and Western blot. A two-tiered protocol is recommended by the Centers for Disease Control and Prevention (CDC): an ELISA test is performed first, and if it is positive or ambiguous, then a Western blot is run. The reliability of testing in diagnosis remains debatable. Studies show the Western blot has a specificity of 94-96% for patients with clinical symptoms of early Lyme disease. The initial ELISA test has a sensitivity of about 46-70%. Erroneous test results have been widely reported in both early and late stages of the disease, and can be caused by several factors, including antibody cross-reactions from other infections, such as the Epstein-Barr virus and herpes simplex virus.

Polymerase chain reaction (PCR) tests for Lyme disease have also been developed to detect the presence of *B. burgdorferi* genetic material. PCR tests are more sensitive than ELISAs and Western blots, and can yield definitive results with lower concentrations of spirochetes. However, PCR tests are generally susceptible to false positive results due to poor laboratory technique and can also yield variable results if the spirochete concentration is too low.

Some laboratories offer Lyme disease testing that include urine antigen tests, PCR tests on urine, lymphocyte transformation tests, and immunofluorescence staining to address if cell wall-deficient *B. burgdorferi* are present.

No practical means for detecting the presence of the organism are currently available. The studies mentioned above generally require high titers of either IgM or IgG antibodies to *Borrelia* antigens in order to definitely declare a positive infection. However, the presence of low quantities of these antibodies, as in the early stages of the infection, makes it difficult to obtain a conclusive diagnosis. Further, antibodies are merely a proxy for determining if an actual live infection is present.

One manner in which to overcome the issue of low spirochete concentrations is by obtaining a specimen from a suspected individual and culturing the specimen to increase bacterial amounts. However, culturing of *B. burgdorferi*, as with many other types of spirochete bacteria, has proven to be quite difficult. One reason for this difficulty includes the inability of *Borrelia* species to tolerate oxygen. *B. burgdorferi* is microaerophilic, meaning it can tolerate only a very small amount of oxygen. Additionally, the spirochetes have very slow reproduction rates and may hide in tissues, making it difficult to collect a sufficient amount of spirochetes to culture. As a result of these issues, the culturing of *Borrelia* species is a challenging process that requires a very complex growth medium. Additionally, spirochetes typically need to be cultured for 3-4 weeks before diagnostic tests or genotyping can be performed. This is unlike most other bacterial species, where culturing only takes hours and testing often can be done within 24-48 hours.

The ability to culture this bacterium would offer the strongest of all proofs that an infection is present. As such, there is a need in the art for diagnostic methods that allow for the accurate and early detection of Lyme disease.

SUMMARY

Detection and diagnosis of Lyme disease has proven problematic for the above mentioned reasons.

Provided herein are a method and a kit useful for obtaining and culturing *Borrelia* spirochetes, such as *B. burgdorferi* strains. The methods and kits allow a patient to easily self-collect specimens, e.g., at home, with no requirement for specialized equipment. The method and kit allow a specimen to be shipped, without deterioration, at temperatures that are typically not considered to be optimal for spirochete bacterial growth and/or amenable for spirochete survival, and the specimens are found to be stable under these conditions for long periods of time, for example, by shipment via a ground courier. The method and kit described here has been shown to have an excellent success rate and to have efficacy towards different strains of *Borrelia*. Added benefits of the described method and kit are the lack of requirement for specialized equipment and low cost.

In one aspect, a method of culturing *Borrelia* spirochetes, such as *B. burgdorferi* from a non-sterile specimen is provided. The method comprising: inoculating spirochete-supportive complete media in a culture vessel with a sample containing, or which is being tested to contain, *Borrelia* spirochetes, where the medium in combination with the sample fills a sufficient percentage, e.g. at least 95%, of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes; sealing the culture vessel with an airtight cap or plug; storing and/or shipping the culture vessel for a time period of at least 8, 12, 24, 30, 36, 42, or 48 hours in uncontrolled environmental conditions, where at least temperature of the culture vessel is not controlled; and culturing the sample in the culture vessel in a controlled environment suitable for culture of *Borrelia* spirochetes, thereby expanding a population of a *Borrelia* spirochete in the sample. In one example, the *Borrelia* spirochete is a *B. burgdorferi* spirochete.

In another aspect, a method of obtaining and culturing *Borrelia* spirochetes, such as *B. burgdorferi* spirochetes from a non-sterile specimen also is provided. The method comprising: receiving from a person a culture vessel comprising a non-sterile biological sample containing, or to be tested for the presence of, *Borrelia* spirochetes, the culture vessel comprising a spirochete-supportive complete medium, where the medium in combination with the sample fills a sufficient percentage, e.g., at least 95%, of the volume capacity of the culture vessel to produce a microaerobic environment, the spirochete-supportive complete media comprising spirochete-supportive media, antimicrobially-effective amounts of a broad-spectrum antibiotic and a bactericidal antibiotic drug, antifungally-effective amounts of an antifungal agent, and serum in amounts effective to support specific growth of *Borrelia* spirochetes, wherein the culture vessel has been stored and/or shipped for a time period of at least 8, 12, 24, 30, 36, 42, or 48 hours in uncontrolled environmental conditions where at least temperature of the culture vessel is not controlled; culturing the sample in the culture vessel in a controlled environment suitable for culture of *Borrelia* spirochetes, thereby expanding a population of *Borrelia* spirochetes present in the sample, or if present in the sample; and determining if *Borrelia* spirochetes have grown in the culture medium by looking for the presence of spirochetes, using microscopy methods, immunological methods, PCR and/or real time PCR, or any suitable equivalent genetic testing for the presence of *Borrelia*, e.g., *B. burgdorferi* specific genes, and/or immunofluorescence or immunostaining assays that look for *Borrelia* spirochetes, such as *B. burgdorferi* specific proteins. The method optionally further comprises, prior to receiving the sample, shipping to the person a kit for obtaining a sample that contains or is to be tested to contain *Borrelia* spirochetes, the kit comprising: sterile spirochete-supportive complete media in a culture vessel, where the medium in combination with a sample fills at least 95% of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes; a pipet, a sterile swab, a sterile disposable scalpel, a disinfecting swab and a sterile sample collection vessel; a return shipping package adapted to receive the culture vessel; and optionally indicia including instructions indicating how to properly store the kit and also how to collect a specimen for inoculation of the media. In one example, the *Borrelia* spirochete is a *B. burgdorferi* spirochete.

In another aspect, also provided herein is a kit for obtaining a sample that contains or is to be tested to contain *Borrelia* spirochetes, such as *B. burgdorferi* cells. The kit comprises: sterile spirochete-supportive complete media in a culture vessel, where the medium in combination with a sample fills a sufficient percentage, e.g., at least 95% of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes; a pipet, a sterile swab, a sterile disposable scalpel, a disinfecting swab and a sterile sample collection vessel; a return shipping package adapted to receive the culture vessel; and optionally indicia including instructions indicating how to store the kit and how to collect a specimen for inoculation of the media. In certain embodiments, the sample is semen and the kit comprises a sterile sample vessel for collecting the semen and a pipet for dispensing semen into the culture vessel or the sample is vaginal, oral or wound and the kit comprises a swab and/or a scalpel.

In yet another aspect, use of the kit described herein also is provided, in which a non-sterile specimen, needed for testing the presence of *Borrelia* spirochetes, such as *B. burgdorferi* cells, is obtained and cultured. The use comprising: receiving from a person a culture vessel comprising a non-sterile biological sample containing, or to be tested for the presence of, *Borrelia* spirochetes, the culture vessel comprising a spirochete-supportive complete medium, where the medium in combination with the sample fills a sufficient percentage, e.g., at least 95%, of the volume capacity of the culture vessel to produce a microaerobic environment, the spirochete-supportive complete media comprising spirochete-supportive media, antimicrobially-effective amounts of a broad-spectrum antibiotic and a bactericidal antibiotic drug, antifungally-effective amounts of an antifungal agent, and serum in amounts effective to support specific growth of *Borrelia* spirochetes, wherein the culture vessel has been stored and/or shipped for a time period of at least 8, 12, 24, 30, 36, 42, or 48 hours in uncontrolled environmental conditions where at least temperature of the culture vessel is not controlled; culturing the sample in the culture vessel in a controlled environment suitable for culture of *Borrelia* spirochetes, thereby expanding a population of *Borrelia* spirochetes present in the sample or if present in the sample; and determining if *Borrelia* spirochetes have grown in the culture medium by looking for the presence of spirochetes, using microscopy methods, PCR and/or real time PCR, or any suitable equivalent genetic testing for the presence of *Borrelia* spirochetes, such as *B. burgdorferi* specific genes, and/or immunofluorescence or immunostaining assays that look for *Borrelia* spirochetes, such as *B. burgdorferi* specific proteins. In one example, the *Borrelia* spirochete is a *B. burgdorferi* spirochete.

In various aspects of the kit, uses for the kit and methods in all embodiments described above and herein, examples of a suitable spirochete-supportive media is selected from the group consisting of BSK-H, BSK-II and MKP. Non-limiting examples of the broad-spectrum antibiotic include one or more of ampicillin, streptomycin, levofloxacin, gatifloxacin, moxifloxacin, ciprofloxacin, phosphomycin, and mixtures thereof and/or the broad-spectrum antibiotic is present in the spirochete-supportive complete media at a concentration between 0.01 mg/ml-0.03 mg/ml. Non-limiting examples of the bactericidal antibiotic drug include one or more of rifabutin, rifapentine, rifaximin, and rifampicin and mixtures thereof, and/or the bactericidal antibiotic drug is present in the spirochete-supportive complete media at a concentration between 0.04 mg/ml-0.06 mg/ml. Non-limiting examples of the antifungal include one or more of amphotericin B, candicidin, filipin, hamycin, natamycin, nystatin, and rimocidin, fluconazole, itraconazole, miconazole, terbinafine and mixtures thereof, and/or the antifungal agent is present in the spirochete-supportive complete media at a concentration between 0.0010 mg/ml-0.0040 mg/ml. The suitable cell culture serum includes one or more of fetal bovine serum, fetal calf serum, horse serum, rabbit serum, chicken serum, caprine (goat) serum, human serum, ovine (sheep) serum, and porcine (pig) serum and mixtures thereof and/or the concentration of cell culture serum is between 5% and 10% of the final volume of the spirochete supportive complete medium. The medium in combination with a sample fills from 95% to 100% or from 99% to 100% of the volume capacity of the culture vessel.

Also, in one aspect, a method of identifying the presence of a spirochete in a biological specimen is provided, comprising: placing the biological specimen suspected of containing a spirochete, or containing a spirochete, such as blood, on a microscope slide; placing a cover slip on the biological specimen on the microscope slide; and sealing edges of the cover slip with a polymer in an organic solvent. In one aspect the polymer in an organic solvent is nail polish, e.g., clear nail polish, for example nitrocellulose in an organic solvent, such as an acetate-based solvent, such as ethyl acetate or butyl acetate.

DETAILED DESCRIPTION

Figure 1A:
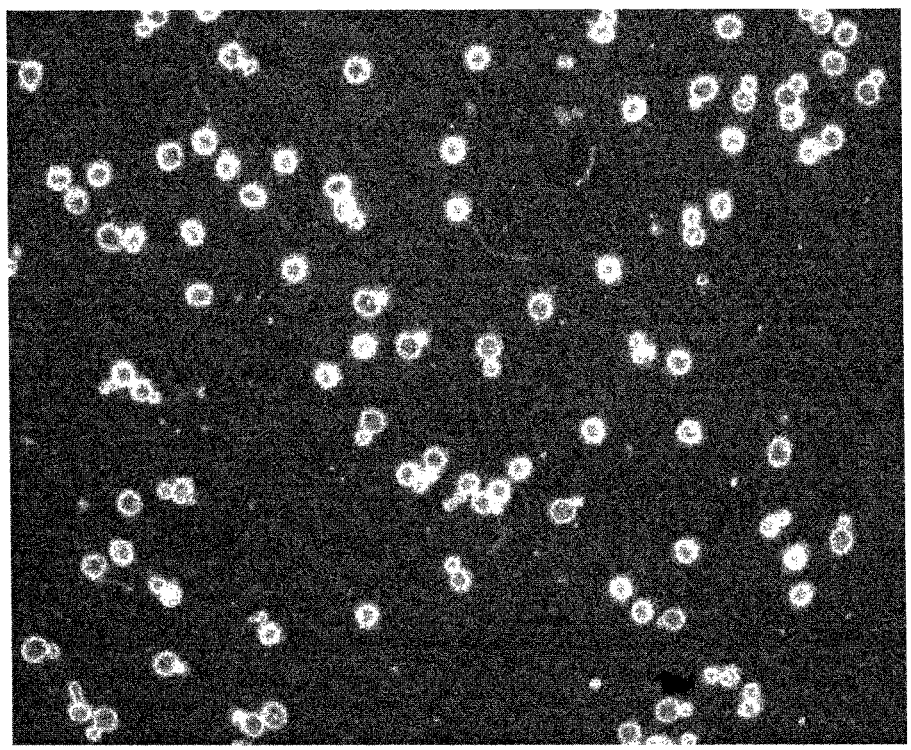
FIGS. 1A and 1B are photomicrographs of blood samples prepared according to Example 2, using thin blood smears (see below).

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are meant to be open ended. The terms "a" and "an" refer to one or more.

As used herein, the term "patient" or "subject" refers to members of the animal kingdom including but not limited to human beings and "mammal" refers to all mammals, including, but not limited to human beings.

As used herein, the term "sample" or "specimen" refers to any material that is submitted to test for the presence of a *Borrelia* spirochete, such as *B. burgdorferi* infection. For example, "samples" or "specimens" include insects, such as deer ticks, or biological materials such as vaginal or seminal fluids, periodontal fluids, blood, and/or materials obtained from an open ulcerative skin lesion.

As used herein, the terms "an individual suspected of having Lyme disease" or "suspected individual" refers to individuals who may have contracted Lyme disease or any other *Borrelia* infection, for example due to being in an area suspected of having a high prevalence of *Borrelia* strains such as parts of the USA, central Europe or Asia, the individual found a black-legged tick on or around his/her body, the individual is speculated to have contracted the disease through sexual transmission, or engaged in any other activity that increased the chances of contracting the disease. For example, being in a wooded area where there is a high deer population.

The term "anaerobic" refers to an environmental condition in which oxygen is not present. Anaerobic conditions include conditions completely devoid of oxygen and conditions with very minute concentrations of oxygen (i.e. "microaerobic" conditions). Microaerobic conditions include conditions with oxygen concentration less than 20%, such as 0-5%, 0-10%, or 0-15%. Microaerobic conditions include conditions with 1%, 2%, 3%, 4%, 5%, 6%, 7%, 8%, 9%, 10%, 11%, 12%, 13%, 14%, 15%, 16%, 17%, 18%, or 19% oxygen, and increments therebetween.

The term "spirochete" refers to a phylum of gram-negative bacteria characterized by a long, helical-coil shape. There are several genera of spirochetes, such as *Borrelia, Treponema, Brachyspira* and *Leptospira*. Non-limiting examples of spirochetes include *Borrelia afzelii, Borrelia anserine, B. burgdorferi* (such as *B. burgdorferi* sensu lato), *Borrelia garinii, Borrelia hermsii, Borrelia recurrentis, Borrelia valaisiana, Borrelia vincentii, Brachyspira aalborgi, Brachyspira pilosicoli, Leptospira alexanderi, Leptospira bflexa, Leptospira broomii, Leptospira borgpetersenii, Leptospira fainei, Leptospira inadai, Leptospira interrogans, Leptospira kirschneri, Leptospira licerasiae, Leptospira meyeri, Leptospira noguchii, Leptospira santarosai, Leptospira weilii, Leptospira wolbachii, Leptospira kmetyi, Leptospira wolffii, Leptospira genomospecies* 1, *Leptospira genomospecies* 3, *Leptospira genomospecies* 4, *Leptospira genomospecies* 5 and *Treponema pallidum*.

The term "spirochete-supportive medium" refers to cell culture medium formulated to promote the growth of spirochetes in culture. Such media are known in the art. Non-limiting examples of spirochete-supportive medium include Barbour-Stoenner-Kelly II (BSK II) medium; MKP medium; and modified BSK medium (BSK-H).

Spirochete-supportive medium typically contains N-acetyl-glucosamine, yeast extract, amino acids, nucleotides, and serum, but various formulations modifying the amount, the addition, or the elimination of specific chemical ingredients have been generated. The original formulation of BSK II medium made by Barbour and Kelly contained, in 1000 ml of medium: 1×CMRL 1066 cell-growth medium without glutamine, 5 g Neopeptone, 50 g bovine serum albumin, 2 g Yeastolate, 6 g HEPES, 5 g glucose; 0.7 g sodium citrate; 0.8 g sodium pyruvate; 0.4 g N-acetylglucosamine, 2.2 g sodium bicarbonate, and adjusted to a pH of 7.6 with 1 N NaOH. Additionally, in the original formulation 200 ml of 7% gelatin and 6% rabbit serum was added. There are slight variations of BSK II medium, as it is not commercially available (Barbour, AG, "Isolation and Cultivation of Lyme Disease Spirochetes (1984) *Yale Journal of Biol. Med.* 57:521-525).

One liter of basic MKP medium contains: 1×CMRL 1066 without glutamine, 3.0 g of Neopeptone, 6.0 g HEPES; 0.7 g citric acid, 3.0 g glucose, 1.8 g pyruvic acid, 0.4 g N-acetylglucosamine, 2.0 g sodium bicarbonate, adjusted to a pH of 7.6 with 5N NaOH (as provided and suggested by a Qiagen protocol to grow *Borrelia* species, see also Ružić-Sabljić E, et al. "Comparison of growth of *Borrelia afzelii, B. garinii*, and *B. burgdorferi* sensu stricto in MKP and BSK-II medium" (2004) *Int J Med Microbiol.* 294(6):407-412). Like BSK II commercial compositions of MKP medium are not available so slight variations may exist. Additionally, reports have shown the addition of gelatin and rabbit serum to MKP medium.

R J Pollack et al. modified the BSK II medium to exclude gelatin and modified various components in proportions that varied from the original medium (Pollack, R J, et al., "Standardization of Medium for Culturing Lyme Disease Spirochetes" (1993) *Journal of Clinical Microbiology* 31(5): 1251-1255). This medium is now known as BSK-H.

In general, as mentioned above, suitable spirochete-supportive medium typically includes a combination of: yeast extract, amino acids/proteins/peptides, nucleosides, glucose, various vitamins, and N-Acetyl-D-Glucosamine which is an essential element of the bacterial peptidoglycan. Forms of BSK-II, MKP, and BSK-H are all suitable media. Examples of suitable, commercially available, spirochete-supportive medium include: BSK-H medium from HiMedia (cat # M1668, Mumbai, India), BSK-H medium from Sigma-Aldrich (cat # B8291, St. Louis, Mo.), or BSK-H medium from Bio-Sell (cat # BS 2.10T02J, Feucht, Germany). Furthermore, to prevent the growth of non-*Borrelia* microbial species, the spirochete-supportive medium is supplemented with a broad-spectrum antibiotic, a bactericidal antibiotic drug, and an antifungal agent. The broad-spectrum antibiotic and the bactericidal antibiotic drug is included in "antimicrobially-effective amounts," and the antifungal agent is included in "antifungally-effective amounts". That is, the amount of the broad-spectrum antibiotic and the bactericidal antibiotic drug prevents, inhibits or reduces the growth of non-*Borrelia* microbial species and the antifungal agent prevents, inhibits or reduces the growth of any fungal species. For stock solutions, antibiotics, antifungals, etc. are be dissolved in any suitable solvent, such as 50% dimethyl sulfoxide (DMSO). Finally the medium is also supplemented with a suitable cell culture sera to help promote *Borrelia* growth.

Herein, "spirochete-supportive complete medium" refers to a spirochete-supportive medium supplemented with a broad-spectrum antibiotic, a bactericidal antibiotic drug, an antifungal agent, and finally a suitable serum for cell culture. A "broad-spectrum antibiotic" refers to an antibiotic that acts against a wide range of disease-causing bacteria. A broad-spectrum antibiotic acts against both Gram-positive and Gram-negative bacteria, in contrast to a narrow-spectrum antibiotic, which is effective against specific families of bacteria. Broad-spectrum antibiotics include, but are not limited to ampicillin, streptomycin, levofloxacin, gatifloxacin, moxifloxacin, ciprofloxacin, and phosphomycin. In addition, wherein any antimicrobial or antifungal chosen for use in the culture methods and kits described herein, the spirochete to be tested is resistant to the chosen antimicrobial or antifungal, meaning that the spirochete will grow in medium containing antimicrobial or antifungal amounts, respectively, of the antimicrobial or antifungal under pertinent culture conditions. A "microbe", e.g., as referred to in an "antimicrobial," refers to a single-cell organism, including bacteria and single-cell fungi.

Suitable final concentrations of the broad-spectrum antibiotic in the spirochete-supportive medium include, but are not limited to, from 0.005 mg/ml to 0.1 mg/ml, for example 0.01 mg/ml, 0.015 mg/ml, 0.02 mg/ml, 0.025 mg/ml, 0.03 mg/ml, and increments therebetween.

Suitable concentrations, or amounts of any specified antimicrobial composition, antifungal composition or sera, can be determined empirically by those of ordinary skill, by culture of non-sterile samples according the a method described herein, e.g., by determining if cells of a *Borrelia* species in e.g., a semen sample can be shipped in the medium containing the material, and later be cultured under controlled conditions suitable for growth of the *Borrelia* species in the medium.

Bactericidal antibiotics kill bacteria. Some drugs of this class function by inhibiting bacterial DNA-dependent RNA synthesis by inhibiting bacterial DNA-dependent RNA polymerase. Rifamycins inhibit the bacterial RNA polymerase, preventing transcription, and are able to penetrate well into cells and tissues. Examples include, but are not limited to, rifabutin, rifapentine, rifaximin, and rifampicin. As above, the spirochete to be tested is resistant to the bactericidal antibiotic chosen.

Suitable final concentrations of the bactericidal antibiotic in the spirochete-supportive medium include, but are not limited to, from 0.025 mg/ml to 0.1 mg/ml, for example 0.04 mg/ml, 0.045 mg/ml, 0.05 mg/ml, 0.055 mg/ml, 0.06 mg/ml, and increments therebetween.

Herein, antifungal reagents refer to compositions that are able to kill or inhibit growth of fungi or fungal spores. As an example, polyene antifungals, specifically, bind with sterols in the fungal cell membrane, principally ergosterol. As a result, the cell's contents including monovalent ions ($K^+$, $Na^+$, $H^+$, and $Cl^-$), small organic molecules leak, ultimately leading to fungal cell death. Animal cells contain cholesterol instead of ergosterol and so they are much less susceptible. Examples of polyene antifungals include, but are not limited to, amphotericin B, candicidin, filipin, hamycin, natamycin, nystatin, or rimocidin. Other antifungals include, for example: fluconazole, itraconazole, miconazole, terbinafine and similar non-polyene compounds.

Suitable final concentrations of the antifungal agent in the spirochete-supportive medium, for example a polyene antifungal, include but are not limited to, from 0.001 mg/ml to 0.1 mg/ml, for example 0.0010 mg/ml, 0.0015 mg/ml, 0.0020 mg/ml, 0.0025 mg/ml, 0.0030 mg/ml, 0.0035 mg/ml, 0.0040 mg/ml, and increments therebetween.

Several cell culture sera are known in the art. Any suitable cell culture sera may be used in the spirochete culture medium. Examples of the serum include: fetal bovine serum, fetal calf serum, horse serum, rabbit serum, chicken serum, caprine (goat) serum, human serum, ovine (sheep) serum, and porcine (pig) serum. The concentration of serum will typically range between from about 5% to 10%, for example 5%, 6%, 7%, 8%, 9%, 10%, or any increment therebetween.

One example of a spirochete-supportive complete medium is BSK-H medium (e.g. purchased from Sigma-Aldrich, Cat # B8291, St. Louis, Mo.), supplemented as follows: the broad-spectrum antibiotic is phosphomycin, the bactericidal antibiotic is rifampicin, the antifungal agent is amphotericin B, the serum is rabbit serum and wherein the final concentration, in the medium, of phosphomycin is 0.02 mg/ml, rifampicin is 0.05 mg/ml, amphotericin B is 0.0025 mg/ml of medium, and rabbit serum is 6%.

To "inoculate" means to introduce a specimen into an environment that is suitable for growth of any cell, tissue, organ etc. For example, the introduction of a microbial species, such as a *Borrelia* species, into a medium that is spirochete-supportive.

To expand a population of microbial cells, such as *B. burgdorferi*, means to place the microbial cells, such as from a sample or specimen, in an environment that is suitable for the growth and/or propagation of the cells, such as in spirochete-supportive complete medium.

A "collection vessel" refers to a sterile piece of laboratory equipment that can either be glass or plastic, having a short, cylindrical shape, and also having a screw top, snap top, or plug top. The containers have a diameter of at least 50 mm. Suitable, non-limiting examples of collections vessels, include but are not limited to those available from The Lab Depot (Cylindrical Jars with Screw Caps, HDPE), Thermo Scientific, or VWR (Nalgene, wide-mouth HDPE bottles with screw caps).

A "culture vessel" refers to a sterile piece of laboratory equipment that can either be glass or plastic, comprising a long, cylindrical shape, of approximately a finger's length, usually having a round U-shaped bottom or even having a pointed V-shaped bottom. In one example, a culture vessel is a vessel that has a screw top allowing for the addition of a cap, enabling the tight sealing-off of the contents contained within the culture vessel. In another example, the culture vessel is sealed with a plug, such as a rubber or silicone plug. Non-limiting examples of culture vessels include: 15 ml sterile Falcon tubes or VACUTAINER™ tubes from BD Diagnostics or evergreen scientific sterile culture tubes with screw caps, commercially available from MedSupply Partners of Atlanta, Ga.

In one embodiment, the culture vessel contains about 85%-99% of spirochete-supportive complete medium. The amount of spirochete-supportive complete medium in the culture vessel is 85%, 86%, 87%, 88%, 89%, 90%, 91%, 92%, 93%, 94%, 95%, 96%, 97%, 98%, 99% or any increment therebetween.

A pipet refers to pipette droppers, which are commonly known in the art. They function by sucking up liquid and are used to transfer liquid materials from one place to another. A useful pipet for the tests and methods described herein has the ability to transfer (the transfer volume of liquid, or transfer capacity of the pipet, commonly referred to as the "volume" of the pipet), for example, 5 ml, 10 ml, or 15 ml of liquid. Non-limiting examples of pipets include: plastic, disposable, transfer pipets available from Heathrow Scientific, disposable droppers from Cole-Parmer, or Nalgene droppers available from Thermo Scientific.

Herein a sterile swab refers to a small piece of absorbent material, such as cotton or gauze, or other woven or non-woven material, wrapped around the end of a wooden, plastic, or metal stick or other suitable substrate, that is used to obtain a biological specimen. Suitable non-limiting examples of sterile swabs, include those available from Fisher Scientific, BD Diagnostics, VWR, Kruuse, FL Medical, or *Avena Medica*.

Herein a sterile disinfectant wipe refers to a small, square shaped, piece of absorbent material, such as cotton or gauze other woven or non-woven material, which has been soaked in alcohol, such as ethanol or isopropanol, or other antimicrobial disinfectants, such as quaternary ammonium antimicrobials, such as benzalkonium chloride, chlorhexidine, gluconate, povidone iodine. Disinfecting wipe, herein, are used to clean the area surrounding the site of specimen collection in order to minimize collection of skin particles or bacteria sitting on the surface of the skin or anything else that may lead to or increase the possibility of false positives. Suitable non-limiting examples of sterile disinfecting wipe, include those available from BD Diagnostics, Curad, or any equivalent of alcohol wipes or disinfecting wipes available.

Herein a sterile scalpel refers to a small surgical knife with a convex or concave sharp edge. Suitable non-limiting examples of sterile disposable scalpels, include those available from Fisher Scientific, Cole-Parmer, VWR, or Kent Scientific.

An indicia is a printed object, such as a label, insert, pamphlet, booklet, leaflet, etc. comprising images and/or type. In the context of a kit provided herein, an indicia provides instructions for kit storage, for example if the kit is not to be used immediately, and additionally instructions for proper collection of the specimen. Indicia can provide URLs for access to instructions via an internet browser, such as Safari, MS-Explorer or Firefox, among others. For example, the indicia will contain instructions that indicate that if the kit is not to be used for a long period of time (i.e., for several months), then the spirochete-supportive medium, should be removed and placed in the freezer and if the kit will be used soon or within a couple of days, the medium may be kept at room temperature or in the refrigerator. In the examples provided below, are exemplary instructions for sample collection that may be included in an indicia included in the herein provided kit.

In one example, seminal secretions are self-collected as follows: semen is collected in a sterile collection vial, the cap of the culture vessel is loosened so it is ready to receive the seminal specimen, semen is transferred by drawing up a substantial amount of semen with a pipet, the semen is then transferred to the spirochete-supportive complete medium, for example BSK-H medium supplemented with a broad-spectrum antibiotic, a bactericidal antibiotic drug, an antifungal agent, and a suitable cell culture sera, in the culture vessel. The emptied pipet is discarded and the cap of the culture vessel is screwed on tightly, or otherwise plugged, so that it is airtight and leak-proof, thus creating a microaerobic environment. In one example, the transfer volume of the pipet, when added to the volume of the spirochete-supportive complete medium in the culture vessel equals approximately 95%-100%, for example 99%-100%, or 100% of the volume capacity of the culture vessel.

In another example, vaginal secretions are self-collected as follows: the cap of the culture vessel is loosened so it is ready to receive the specimen, the patient is requested to then spread apart labia and to insert a sterile swab into the vagina so that it will be coated with vaginal secretions. The swab is then gently agitated into the culture vessel containing the spirochete-supportive complete medium, for example BSK-H medium supplemented with a broad-spectrum antibiotic, a bactericidal antibiotic drug, an antifungal agent, and a suitable cell culture sera. The swab is discarded and the cap of the culture vessel is screwed on tightly, or otherwise plugged, so that it is airtight and leak-proof, thus creating a microaerobic environment. The amount of the spirochete-supportive complete medium in the culture vessel is approximately, 95%-100% or 100% of the volume capacity of the culture vessel.

In one embodiment, oral specimens are collected as follows: fluid from the periodontal pockets are expressed and obtained by applying pressure with a finger to the oral gum tissue directly above a tooth or teeth, the fluids are then obtained by applying slight pressure, with a sterile swab, to the junction between the tooth and gum to collect fluid expressed from the periodontal pockets. The swab is then gently agitated into the culture vessel containing the spirochete-supportive complete medium, for example BSK-H medium supplemented with a broad-spectrum antibiotic, a bactericidal antibiotic drug, an antifungal agent, and a suitable cell culture sera. The swab is discarded and the cap of the culture vessel is screwed on tightly, or otherwise plugged, so that it is airtight and leak-proof, thus creating a microaerobic environment. The amount of the spirochete-supportive complete medium in the culture vessel is approximately, 95%-100% or 100% of the volume capacity of the culture vessel.

In another embodiment, skin specimens are collected as follows: the lesion and surrounding area is cleaned by quickly swabbing the area, with a disinfecting swab, to partially remove normal superficial skin flora; a sterile disposable scalpel is then scraped against the skin to remove skin flakes; the skin flakes are then swabbed with a sterile swab and introduced into the spirochete-supportive complete medium, for example BSK-H medium supplemented with a broad-spectrum antibiotic, a bactericidal antibiotic drug, an antifungal agent, and finally a suitable cell culture sera. The swab is then gently agitated into the culture vessel, discarded and the cap of the culture vessel is screwed on tightly, or otherwise plugged, so that it is airtight and leak-proof, thus creating a microaerobic environment. The amount of the spirochete-supportive complete medium in the culture vessel is approximately, 95%-100% or 100% of the volume capacity of the culture vessel.

Collected samples are then processed in a suitable healthcare facility. For example, the samples may be mailed back to a suitable diagnostic laboratory capable of efficiently processing and analyzing the collected samples.

Mailing, herein, refers to standard mailing procedures and practices. The collected specimen is placed in a suitable protective package, and is labelled appropriately. A return shipping package adapted to receive a culture vessel may be anything that is large enough and provides sufficient protection to the culture vessel. Suitable, non-limiting, examples include foam boxes, such as styrofoam, cardboard boxes, or thick-cardboard-like shipping/mailing envelopes. The herein described kit is an example comprising a suitable shipping package.

Mailing of the collected specimen to the diagnostic lab can be done through suitable carriers, such as, FedEx, United Parcel Services, DHL, or the United States Postal Service.

In one example, a mailing label that indicates the location to which the specimen will be sent and the carrier will be provided as part of the kit contents.

Herein, mailing of the samples refers to the inoculated cultures being maintained in an uncontrolled environment characteristic of standard shipping procedures typically, but not exclusively for 48 hours, for example, for anywhere between 8-96 hours. Durations of time that the cultures are maintained in an uncontrolled environment include: 8 hours to two weeks, 8 hours to one week, 8 hours to 48 hours, 8 hours to 36 hours, for example 8, 9, 10, 11, 12, 13, 14, 15, 16, 17, 18, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48 hours, or any time increment in between. An uncontrolled environment, is defined herein, as conditions in which environmental temperature, humidity, and/or $CO_2$ levels are not controlled, and therefore, the conditions are not necessarily optimal for spirochete growth. Uncontrolled environmental conditions do not mean that the packaging for the collected sample(s) is not insulated or insulating. Conditions include temperatures ranging from below 0° C. or from 0-41° C. or room temperature (e.g., from 15° C. to −25° C.).

In one example, a kit is provided herein including the following contents: indicia providing instructions upon arrival indicating proper storing methods, a sterile collection vial, a sterile disposable pipette, a sterile swab, a sterile disinfecting wipe, a sterile disposable scalpel, a culture vessel with sterile complete BSK-H liquid medium, filled, e.g., to at least 85% of its volume capacity, indicia further provides instructions on how a patient should properly obtain the desired specimen, suitable shipping package along with an addressed mailing slip. In one example, the culture vessel is mailed to the patient either with ice, dry ice, a cold-pack, or any equivalent thereof to ensure that the culture medium contained within the culture vessel remains frozen.

Once a healthcare facility, lab, (e.g. diagnostic lab), or any other suitable facility has received the specimen. The specimen is then cultured in a controlled environment, for example in a laboratory. A controlled environment, herein, refers to conditions that are suitable for, and perhaps optimal, for spirochete growth. A "controlled environment" does not refer to transient environmental conditions found during transfer of the specimen from the collection site to the culturing site, such as in a storage or distribution facility, or in a shipping vehicle, such transient environmental conditions that are not set for the purpose of culturing bacterial specimens. Thus, "controlled" and "uncontrolled" are contextual, referring to the purposeful establishment of conditions suitable for bacterial growth and/or placement of the culture in a temperature-controlled environment for the purpose of bacterial growth, and/or in the context of shipping a specimen via common carriers as opposed to actions taken with the specific goal of culturing the specimen, such as placement in an incubator or warm room, or placement on a laboratory bench or shelf in which temperature is both controlled, and the placement is for the purpose of expanding the cell population. In one example, the culture vessels are incubated in an incubator or water bath that is maintained at 26-37° C., for example in a 32° C. incubator, water bath or room. In one example, the specimen is cultured in a warm room from 26° C. to 37° C. Although variation from the following can often result in microbe growth, suitable culture conditions include a temperature range between 26° C. and 37° C., including these temperatures and any increment between the two temperatures. Putting the cultures in a 5% $CO_2$ or anaerobic chamber can enhance growth, but is not required. In one embodiment, the tube is topped up, to approximately 100% of the tube volume, with medium after it arrives, to minimize the air space in the tube in order to provide an anaerobic or microaerobic environment. It is typically preferable not to agitate the tube, so as to prevent distribution of $O_2$ in the medium. The cultures are incubated for at least one day, and more typically for at least one, two, or three weeks, for example for one week or for one month, though longer culture times may be required in instances. Cultures are examined routinely, for example once or twice a week, for growth of microbes. Of note, blood cultures take longer to grow as compared to genital or oral cultures, which usually produce detectable growth within one week.

BSK medium includes a color indicator. When enough growth is present then color of the medium changes to yellow. In blood cultures this does not usually occur as there is very little growth. But the color turns yellow very often in the semen and vaginal (genital) cultures as described herein. The medium sometimes becomes turbid, or sometimes it is clear with a precipitate at the bottom of the tubes. Viewing the organism with darkfield at 400× or better, assists in determining growth and morphology of the organism. As indicated herein, spirochetes grow more rapidly and healthier from periodontal spaces and from genital secretions than from blood. Growth of visible organisms is common and PCR or other molecular diagnostic often is required to characterize the type of growth.

Upon culturing of the specimen various options exist for the detection of *Borrelia* and diagnosis of Lyme disease. For example, the cultures are checked for spirochetes. This can be done by various methods. The goal of this step is to make sure that the spirochetes grew. Isolating the bacteria and checking under a bright- or dark-field microscope for spirochetes would be sufficient. Upon confirmation that the spirochetes grew, the sample can then be further processed to molecularly identify the spirochete bacteria. Molecular identification of the spirochete bacteria will allow for confirmation of presence of *Borrelia* and also will allow for the identification of the specific type of strain. The lab that is preforming the molecular identification of the bacteria must contain suitable equipment and reagents to perform such tests. The types of tests used in the detection of *B. burgdorferi* are discussed below, however, in general, molecular diagnostic labs should be able to perform either PCR, immunofluorescence, ELISAs, or immunostaining/Western blots. Capacity to perform more than one of these tests is preferable.

In one example, the live culture is examined for the presence of spirochetes using a dark-field microscope or a fluorescent microscope. In another example, a portion of the cells in the culture are stained. In one example, the cells are stained with Dieterle stain, which employs silver nitrate and uranium nitrate to detect the presence of spirochetes. In another example, a Warthin-Starry silver nitrate stain is used. In yet another example, cells from the culture are immunostained, for example, with an antibody directed to whole cell preparations of *B. burgdorferi* (anti-*B. Burgdorferi* antibody, or to spirochete-specific markers, such as flagella, ospA and ospC. Immunostaining assays may be performed either with an ELISA test, Western blot, or immunofluorescence assays. In one example, the spirochetes are immunostained first by conjugation with an anti-*Borrelia*, or an anti-*B. burgdorferi* antibody (primary antibody), and then bound antibody is detected with a labeled antibody directed to the bound antibody (secondary antibody). For example, if the anti-*B. burgdorferi* antibody is a rabbit IgG, then the labeled antibody is an anti-rabbit IgG antibody labeled with a detectable tag, such as a fluorochromes (fluorophores), for example and without limitation fluorescein isothiocyanate (FITC)-labeled goat anti-rabbit IgG antibody or enzyme-labeled antibody, such as alkaline phosphatase or horseradish peroxidase-labeled anti-rabbit IgG antibody. Bound fluorochrome is detected by fluorescence and bound enzyme is detected by action on a substrate, such as colorimetric assay. A very large number of labels tags, secondary antibodies, etc, such as fluorochrome-labeled secondary antibodies and enzyme-labeled secondary antibodies and suitable substrates therefor are broadly known in the medical and diagnostic arts, and choice of such labels and suitable antibodies and combinations thereof are within the skill of an ordinary artisan. In another example, DNA is extracted from the cells of the culture for PCR. The PCR may be performed with spirochete-specific primers, such primers may amplify 16S rRNA/rDNA, flagella, rpoC, uvrA, ospA or ospC encoding sequences or housekeeping genes, such as *Borrelia* GAPDH, or any other suitable gene that is specific to the *Borrelia* spirochete.

EXAMPLES

The present invention will be described in part in the following Example(s). However, the invention should not be considered so limited, and should instead be defined by the appended claims.

Materials and Methods:

1) A 100× stock antibiotic solution was prepared containing phosphomycin (2 mg/ml), rifampicin (5 mg/ml), and amphotericin B (0.25 mg/ml) (Sigma-Aldrich) in 50% water and 50% Dimethylsulfoxide (Sigma-Aldrich).

2) Modified BSK-H medium was prepared as follows: The stock antibiotic solution was filter-sterilized using a sterile PTFE 0.20 μm syringe filter (Millipore) and added to sterile Barbour-Stoner-Kelly H (BSK-H) complete medium, with 6% rabbit serum (Sigma Aldrich, # B8291) using 1 ml stock to 100 ml BSK-H so that antibiotics were present in solution at a final concentration of 0.02 mg/ml phosphomycin, 0.05 mg/ml rifampicin, 0.0025 mg/ml amphotericin B, and 6% rabbit serum.

3) Sterile modified BSK-H medium was aseptically distributed to sterile 8 ml polystyrene screw-cap culture vessels so that only a small airspace (<0.5 ml) remained at the top. Vessels were frozen until day of inoculation.

4) For inoculation: On the day of inoculation, culture vessel with frozen liquid culture medium was thawed, by the patient, at room temperature over at least one hour. Patients were instructed to open the vessel for as little time as possible to minimize contamination with particles in the air. Participants were also instructed to wash collection sites thoroughly with soap and water to minimize contamination by skin bacteria. After adding samples, the tops of culture vessel were screwed on tightly, by the patient, so they were airtight and leak-proof, and thereby created a microaerobic environment.

5) After inoculation, the culture vessel was shipped immediately to a laboratory and incubated in an incubator at 32° C. for at least one week and up to six months. The cultures are checked microscopically on a weekly basis.

6) Upon culturing, cultures were concentrated by centrifugation at 15,000 g for 20 minutes, the supernatant discarded, and the culture pellet was formalin-fixed for both Dieterle staining and anti-*B. burgdorferi* immunostaining or was covered with 200 µl of Qiagen A1 lysis buffer (Qiagen). Cultures were first checked for visible spirochetes and further processed for molecular identification.

There are variations to the methods described below. Rather than transport a post-culturing cell pellet in lysis buffer, it can be transported on dry ice with no buffer. For staining, a pellet can be sectioned, or some culture fluid can be smeared on a Superfrost slide, fixed with acetone, and then stained. PCR can be performed using different primers than those described. After culturing, for PCR the cells can be stored, transported processed according to any suitable protocol for obtaining DNA from a spirochete sample.

According to a further aspect, it has been found that by sealing the edges of a cover slip with a polymer/solvent mixture, spirochete organisms migrate out of blood cells and tissue samples, and are visible even though they are not visible or are minimally visible without the polymer/solvent mixture. Thus, according to a further aspect, a method of identifying the presence of a spirochete in a specimen is provided. The method comprises: placing the specimen comprising cells on a microscope slide, where the specimen is either suspected of containing a spirochete, or contains a spirochete; placing a cover slip on the biological specimen on the microscope slide; and sealing edges of the cover slip, or otherwise contacting the specimen with a polymer in a solvent.

In one aspect, the specimen is blood. In another, the sample is tissue, such as a skin culture sample. Examples of the polymer include a film-forming lacquer, such as nitrocellulose polymer dissolved in a volatile organic acid such as butyl acetate or ethyl acetate, for example clear nail polish. An example of a polymer/solvent mixture includes nitrocellulose combined with an acetate, such as ethyl acetate, butyl acetate, or a $C_{1-6}$ alkyl acetate. Optionally, an organic solvent, such as ethyl acetate, butyl acetate, or a $C_{1-6}$ alkyl acetate is simply added to the specimen, e.g. blood, to cause the migration of the spirochetes from the blood cells. In one aspect, the specimen is a tissue sample.

In a further aspect, a method of identifying the presence of a spirochete in a biological specimen is provided, comprising the following: a. placing the biological specimen suspected of containing a spirochete, or containing a spirochete, such as blood, on a microscope slide; b. placing a cover slip on the biological specimen on the microscope slide; c. sealing the edges of the cover slip with a polymer/solvent mixture, such as nitrocellulose in an acetate-based solvent such as ethyl acetate, butyl acetate or a $C_{1-6}$ alkyl acetate; and d. Examination of the slide under a darkfield microscope to identify spirochetes.

The term "alkyl" refers to both branched and straight-chain saturated aliphatic hydrocarbon groups. These groups can have a stated number of carbon atoms, expressed as $C_{x-y}$, where x and y typically are integers. For example, $C_{1-6}$, includes $C_1$, $C_2$, $C_3$, $C_4$, $C_5$, and $C_6$. Alkyl groups include, without limitation: methyl, ethyl, propyl, isopropyl, n-, s- and t-butyl, n- and s-pentyl, hexyl, etc.

Example 1

For purposes of testing the suitability and feasibility of the present invention, various biological samples were obtained and cultured in one of the following three ways: 1) samples were incubated and cultured at 32° C. immediately after inoculation, 2) upon sample inoculation, samples were transported at a less than ideal temperature (e.g., in an uncontrolled environment, samples transported for ~7 days, samples stored in a refrigerator for several months.), and then incubated at 32° C. (e.g., in a controlled environment) upon arrival at the diagnostic laboratory, 3) samples were inoculated and allowed to sit at room temperature until bacterial growth was observed. After bacterial growth was observed, samples were then processed and analyzed to address if *Borrelia* infection was present.

*Borrelia* Culture:

Patients were asked to self-collect samples, as described above. Additionally, in some situations ten milliliters of whole blood was collected by venipuncture and allowed to clot at room temperature for 10 to 15 minutes. Red blood cells (RBCs) were separated by centrifugation at 1,500 g for 15 minutes and the serum, and layers between serum and red blood cells, and some RBCs were used for blood culture inoculum in Barbour-Stoner-Kelly H (BSK-H) complete medium, with 6% rabbit serum (Sigma Aldrich, # B8291) and the following antibiotics: phosphomycin (0.02 mg/l), rifampicin (0.05 mg/l), and amphotericin B (2.5 µg/l) (Sigma-Aldrich). Cultures were conducted by one of the three manners mentioned above. If and when the samples were incubated at 32° C., this was done in an Oxoid anaerobic jar (Thermo Scientific) with an AnaeroGen sachet (Thermo Scientific). Cultures were checked weekly by light and/or dark-field microscopy for visible motile spirochetes. Cultures were concentrated by centrifugation at 15,000 g for 20 minutes, the supernatant discarded, and the culture pellet was formalin-fixed for Dieterle and anti-*B. burgdorferi* immunostaining or was covered with 200 µl of Qiagen A1 lysis buffer (Qiagen).

Polymerase Chain Reaction (PCR) Testing of Cultures

Culture samples were tested using nested PCR detection directed to the *B. burgdorferi* pyrG, Fla, 16S rRNA, and GAPDH genes, and the TaqMan real-time PCR detection of *B. burgdorferi* targeted the 16S rRNA gene. Endpoint PCR also used and was targeted to the rpoC gene. Negative controls included: water, normal human foreskin, normal Morgellons patient's (CC) skin, normal Lyme patient's (MM) skin, normal Lyme patient's (RA) skin. Samples that were used as negative controls underwent PCR with primers targeted against *Borrelia* genes: pyrG, fla, uvrA, OspC, and 16s rRNA.

In further detail, in order to genetically characterize the *B. burgdorferi* strain, the sample is first screened by RT-PCR for the 16S rRNA target and if positive, endpoint PCR amplification and sequencing of the *B. burgdorferi* rpoC gene target from the culture isolate was performed and followed by Basic Local Alignment Search Tool (BLAST) analysis for comparison with known *B. burgdorferi* strain sequences. Noted in the tables are the different strains, the percent sequence match, and the percent query sequence covered (QC).

Nested PCR was used to amplify the *Borrelia* pyrG gene from extracted DNA with the primers targeted to genes as indicated below. The first run of PCR used 20 μl of template DNA in a final reaction volume of 50 μl consisting of 1× Buffer B (Fisher Scientific) with 2 mM $MgCl_2$, 0.4 mM dNTP mix, 2.5 U recombinant Taq polymerase (Invitrogen), and forward and reverse primers at a concentration of 2 μM each. The subsequent run used 1 μl of PCR product from the first reaction. All concentrations remained the same. Both reactions were cycled with the same protocol: 94° C. for 5 minutes, 40 cycles of 94° C. for 1 minute, 48° C. for 1 minute, and 72° C. for 1 minute, with a final extension of 72° C. for 5 minutes.

```
Nested Primer Sequences for pyrG:
Outer primers:                           (SEQ ID NO: 1)
5'-ATTGCAAG1TCTGAGAATA-3',
                                         (SEQ ID NO: 2)
5'-CAAACATTACGAGCAAATTC-3' (762 bp product);

Inner primers:                           (SEQ ID NO: 3)
5'-GATATGGAAAATATTTTATTTATTG-3',
                                         (SEQ ID NO: 4)
5'-AAACCAAGACAAATTCCAAG-3' (663 bp product).
```

PCR—(16S rRNA):

Detection of *B. burgdorferi* by PCR was performed using the Eco™ Real-Time PCR system with software version 3.0.16.0, with primers AB-B1 targeting the *Borrelia* 16S rRNA gene. DNA was extracted from the culture pellet dissolved in 200 μl of Qiagen A1 lysis buffer using the QIAamp DNA Mini Kit (Qiagen). The extracted DNA sample was analyzed in duplicate with positive and negative controls, the thermal profile involved incubation for 2 mins at 50° C., polymerase activation for 10 mins at 95° C. then PCR cycling for 40 cycles of 10 secs at 95° C. dropping to 60° C. sustained for 45 secs.

Immunofluorescence and Immunostaining:

Dieterle silver nitrate stain was performed by standard histological methodology. Anti-*B. burgdorferi* immunostaining and *B. burgdorferi* molecular detection with 2 different *B. burgdorferi*-specific DNA probes that fluoresce upon hybridization with complementary RNA or DNA (molecular beacons), Flagellin bb0147 (Fla probe, FlaB) and BBo 060 (probe 740, p740) pre-engineered by Tyagi and colleagues (Tyagi S, et al. Molecular Beacons in Diagnostics, *F1000 Med. Rep.* 2012; 4:10) were conducted. In addition, formalin-fixed culture pellets were paraffin-embedded and sectioned for Dieterle, anti-*B. burgdorferi* immunostaining and staining with the DNA probes described below.

Immunostaining of the culture pellet sections was performed using an unconjugated rabbit anti-*B. burgdorferi* polyclonal antibody (Abcam ab20950) and then incubated with an alkaline phosphatase probe (Biocare Medical # UP536L) followed by a chromogen substrate (Biocare Medical # FR805CHC) and counterstained with Hematoxylin. Staining was titrated to determine optimal antibody dilutions (1:400) to achieve positive staining of spirochetes while minimizing background staining. Negative controls of culture pellets from mixed Gram-positive bacteria and mixed Gram-negative bacteria were also prepared for comparison purposes to determine possible cross-reactivity with commonly encountered microorganisms.

Upon staining, samples were also examined for the presence of *Treponema pallidum* and *Treponema denticola*. *Treponema pallidum* is a spirochete bacterium with subspecies that cause treponemal diseases such as syphilis. Samples were checked for this to ensure that there was no cross contamination. PCR was performed by Australian Biologics of Sydney Australia.

Scanning Electron Microscopy (SEM)

Glutaraldehyde-fixed samples for SEM were washed in buffer and dehydrated in a graded series of ethanol concentrations. Samples were then immersed in hexamethyldisilazane for 5-15 minutes and air-dried at room temperature. Dried samples were mounted on Al mounts. Samples were not coated but placed into a Hitachi (Tokyo, Japan) TM3000 microscope and imaged in the variable pressure mode (Middelveen M J, Mayne P J, Kahn D G, Stricker R B. Clinical, Cosmetic and Investigational Dermatology 2013, 6:1-21).

Molecular Beacons:

*B. burgdorferi* molecular beacon DNA probes were generously supplied by Dr. Alan MacDonald. DNA probe sequences were subjected to BLAST analysis as part of the initial design to determine specificity. Probe FlaB is derived from the *B. burgdorferi* open reading frame (ORF) BB0147 of the flagellin B gene that contains more than 1000 nucleotides. A sequence of 23 nucleotides was selected from this ORF. A nucleotide Basic Local Alignment Search Tool (BLASTn) search of the 23 nucleotide sequence disclosed no matches in the human genome or in any other lifeform other than that of *B. burgdorferi* BB0147. Probe 740 is derived from the *B. burgdorferi* ORF BB740 that represents a *B. burgdorferi* inner cell membrane protein. A similar BLASTn search produced no matches other than that of the *B. burgdorferi* ORF BB740. Thus a high degree of specificity for *B. burgdorferi* sensu stricto was assured.

*B. burgdorferi* detection with the molecular beacons was performed by the following protocol: Paraffin sections were completely dewaxed by baking at 60° C. and immersion in serial 100% xylene baths, followed by serial immersion through baths of 100% ethanol, 90% ethanol, 80% ethanol, and finally in distilled H2O, then air-dried. Fixed sections were immersed in 20 μl of the working DNA beacon. The sectioned specimen was covered with a thin layer of plastic cut from a Ziploc® freezer bag and was heated at 90° C. for 10 minutes to denature all DNA and RNA. The heat was reduced to 80° C. for 10 minutes, then samples were allowed to gradually cool to 24° C. The slides were washed in PBS, and covered with 30% glycerol and a glass coverslip, then examined under an EPI Fluor microscope. Staining with DNA probes was performed alongside staining of positive and negative controls. The positive control was prepared by embedding a known *B. burgdorferi* strain in agarose, formalin-fixing the specimen then blocking in paraffin and staining sections as described above.

Results:

Table 1 is a one to one comparison comparing blood samples that were incubated and cultured in a controlled environment immediately after inoculation, to self-collected samples that were transported in an uncontrolled environment, after inoculation, and then placed in a controlled environment. Each sample was tested by each of the means described above, unless otherwise noted in the table ("not performed"). As can be seen by the data in Table 1, samples that were self-collected, transported in an uncontrolled environment, and subsequently cultured in a controlled environment only after arrival at a diagnostic lab, showed the presence of *Borrelia* spirochetes in one or more of the assays used. Additionally, it is important to note that it has often been suggested that *Borrelia* infections are not sexually transmitted and that viable spirochetes, capable of growth, can't be obtained from vaginal or seminal secretions. Data herein, not only show that this is not the case, but also that individuals who are suspected of having a *Borrelia* infection, can submit vaginal or seminal specimens with the expectation of receiving reliable results. Data in the table suggests and supports the utility and feasibility of the herein described methods for self-collection of biological samples from patients who are suspected of having a *Borrelia* infection.

Table 2 shows samples that upon inoculation were incubated 3-4 weeks at room temperature with no special treatment. As is shown in Table 2, the negative controls, that is, samples that were known to not have any *Borrelia* infection, did not react positively in any of the assays performed. However, samples obtained from individuals who were suspected have having the disease, showed positive reactivity in one or more of the assays performed.

The data contained in Table 3 function as positive controls. Samples here were obtained, inoculated, and immediately cultured in a controlled environment. As expected, this culturing method worked well and spirochetes were able to grow. Additionally, as in Table 1, data here show that specimens collected from skin lesions, the periodontal, or seminal/vaginal secretions contain viable spirochetes that are capable of growing in a suitable medium. Once again, data here support the utility and easy nature of the methods provided herein for self-collection of biological samples for the testing of Lyme disease.

Samples in Table 4 were obtained, inoculated, transported in an uncontrolled environment and cultured in a controlled environment once received by the diagnostic lab. Data here show that specimens collected from skin lesions, the periodontal, or seminal/vaginal secretions contain viable spirochetes that, by the methods provided herein, survive in the uncontrolled environment and are able to grow once placed in the suitable environment. Data here further support that specimens can be self-collected from various areas of the body, that these specimens can be transported in an uncontrolled environment and after being cultured in a controlled environment show positive reactivity in one or more of the assays performed.

Table 5 contains various negative controls showing that these samples did not exhibit positive reactivity.

Table 6 lists all of the patient samples that were shipped from Canada to Australia, Finland, California, and Connecticut for PCR testing. Patients IDs correspond to patients found in Tables 1-5. Once again, data supports specimens being transported in uncontrolled environments for a prolonged period of time.

Taken together, data strongly suggest that self-collection methods are feasible and may help to solve the problem of false negatives that are currently present in the art.

For Table 1, Antibiotic treatment patients: Doxycycline 100 mg BID; clarithromycin 500 mg BID; cefdinir 300 mg BID; amoxicillin 1 g BID. (patient 2) culture+1 month Doxycycline, then @ 4 months Doxycycline, (3) culture+1 month of clarithromycin and cefdinir, (6, 7), both cultured+1 month doxycycline, switched to clarithromycin and amoxicillin then (7) culture+@ nine months of treatment.

TABLE 1

Data Summary Lyme cultures Comparison of Different specimens collected from the same individual using different culture methods

| Sample ID of culture, type of inoculum (scew cap - microaerobic) (patient number) | Transport and Culture conditions (screw cap - microaerophillic, anaerobic jar) | Microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (Patient 1) blood | 32° C. anaerobic jar | Detected in fluid<br>Detected Dieterle stain<br>Bb immuno (MC)+ | Nested PCR 16S rRNA+<br>Nested PCR Fla+ | 16S rRNA Bbss |
| (1) vaginal | Transported several days variable temperature, screw cap, 32° C. | Detected in fluid<br>Detected Dieterle<br>Bb immuno (MC)+ | Real-time PCR 16S rRNA (AB)+ | |
| (1) vaginal | Transported several days variable temperature, screw cap, 32° C. | Detected in fluid | Real-time PCR 16S rRNA (AB)+ | |
| (2) blood | 32° C. anaerobic | Detected in fluid<br>Detected Dieterle<br>Bb immuno (MC)+ | Nested 16s rRNA+<br>Real-time 16S rRNA (AB)+<br>End point PCR rpoC+ | 16S rRNA BbSS<br>rpoC Bbss |
| (2) semen | Screw cap, 32° C. | Detected in fluid<br>Detected Dieterle<br>Bb immuno (MC)+ | DNA probe 740+<br>Real-time PCR 16S rRNA (UNH)+<br>Nested 16S rRNA+<br>Real-time 16srRNA (AB)+<br>Endpoint rpoC+ | 16S rRNA Bbss<br>rpoC Bbss |
| (2) semen 1 month treatment doxycycline | Screw cap, 32° C. | Detected in fluid<br>Detected Dieterle<br>Bb immuno (MC)+ | | |
| (2) semen 4 months treatment antibiotics | Screw cap, 32° C. | Detected in fluid | Real-time 16srRNA (AB)+<br>Endpoint rpoC+ | rpoC Bbss |
| (2) periodontal | Screw cap, 32° C. | Detected in fluid<br>Detected Dieterle<br>Bb immuno (MC)+ | Real-time 16srRNA (AB)+<br>Endpoint rpoC+ | rpoC *Borrelia* spp. |

TABLE 1-continued

Data Summary Lyme cultures Comparison of Different specimens collected from the same individual using different culture methods

| Sample ID of culture, type of inoculum (scew cap - microaerobic) (patient number) | Transport and Culture conditions (screw cap - microaerophillic, anaerobic jar) | Microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (3) blood | 32° C. anaerobic | Detected in fluid<br>Detected Dieterle stain<br>Bb immuno (MC)+ | Nested PCR pyrG+<br>Nested PCR 16S rRNA+<br>Real-time 16srRNA (AB)+<br>Endpoint rpoC+<br>probe 740+<br>probe FlaB+ | 16S rRNA partial sequence<br>rpoC Bbss |
| (3) vaginal | Screw cap, 32° C. | Detected in fluid<br>Detected Dieterle stain<br>Bb immuno (MC)+ | Real-time PCR 16S rRNA (UNH)+<br>Nested PCR, Fla+,<br>Nested pyrG+,<br>Nested 16SrRNA+<br>Real-time 16srRNA (AB)+<br>Endpoint rpoC+<br>probe 740+<br>probe FlaB+ | rpoC Bbss |
| (3) vaginal 1 month of Omnicef/Biaxin | Screw cap, 32° C. | Detected in fluid<br>Detected Dieterle stain<br>Bb immuno (MC)+ | Real-time 16srRNA (AB)+<br>Endpoint rpoC+ | rpoC Bbss |
| (4) blood | Anaerobic, 32° C. | Detected in fluid<br>SEM | Nested pyrG+<br>Real-time PCR (AB)+ | |
| (4) vaginal | Screw cap, 32° C. | Detected in fluid<br>Bb immuno (UNH)+ | Real-time PCR (UNH)+<br>Real-time 16S rRNA (AB)+<br>Endpoint rpoC+<br>DNA probe 740+ | rpoC Bbss |
| (5) blood | Screw cap, 32° C. | Detected Dieterle stain<br>Bb immuno (MC)+ | Nested Fla+<br>Real-time PCR (UNH)+ | Fla Bbss |
| (5) semen | Screw cap, overnight at room temperature 23° C., then 32° C. | Detected Dieterle stain<br>Bb immuno (MC)+ | Nested Fla+<br>Nested 16S rRNA<br>Real-time PCR 16S rRNA (UNH)+<br>FlaB probe | 16S rRNA *Borrelia* spp. |
| (6) blood | Screw cap, 32° C. | Detected in fluid<br>Detected Dieterle stain<br>Bb immuno (MC)+ | Real-time PCR 16S rRNA (UNH)+<br>Nested FlaB+<br>Real-time 16srRNA (AB)+<br>DNA probe 740+ | |
| (6) seminal | Screw cap, overnight at room temperature 23° C., then 32° C. | Detected in fluid<br>Detected Dieterle stain<br>Bb immuno (MC)+<br>SEM | Real-time PCR 16S rRNA (UNH)+<br>DNA probe 740+<br>DNA probe FlaB+ | |
| (6) seminal on antibiotics doxycycline | Screw cap, overnight at room temperature 23° C., then 32° C. | Detected in fluid<br>Detected Dieterle stain<br>Bb immuno (MC)+ | Nested PCR GAPHD+<br>Real-time 16srRNA (AB)+ | |
| (7) Blood | Screw cap 32° C. | Detected in fluid<br>Detected Dieterle stain<br>Bb immuno (MC)+ | Real-time PCR 16S rRNA (UNH)+<br>Nested pyrG<br>Real-time PCR 16S rRNA (AB)+<br>DNA probe 740+ | |
| (7) vaginal | Screw cap, 24 hours at room temperature 23° C., then 32° C. | Detected in fluid<br>Detected Dieterle stain<br>Bb immuno (MC)+ | Nested GAPHD<br>Real-time PCR 16S rRNA (AB)+<br>DNA probe 740+<br>DNA probe FlaB+ | |
| (7) vaginal on antibiotics doxycycline 1 month | Screw cap, 24 hours at room temperature 23° C., then 32° C. | Detected in fluid<br>Detected Dieterle stain<br>Bb immuno (MC)+ | Nested GAPHD+<br>Real-time PCR 16S rRNA (AB)+<br>Endpoint rpoC+ | rpoC Bbss |
| (7) vaginal on antibiotics 9 months amoxicilin | Screw cap, 24 hours at room temperature, then 32° C. | Detected in fluid<br>Detected Dieterle stain<br>Bb immuno (MC)+ | Real-time PCR 16S rRNA (AB)+ | |
| (8) blood | Screw cap 32° C. | Detected in fluid<br>Detected Dieterle stain<br>Bb immuno (MC)+ | Nested pyrG+<br>Real-time PCR 16S rRNA (AB)+<br>DNA probe 740+ | |
| (8) vaginal | Screw cap, 24 hours at room temperature, then 32° C. | Detected in fluid<br>Detected Dieterle stain<br>Bb immuno (MC)+ | Real-time PCR 16S rRNA (UNH)+<br>Nested pyrG+<br>Real-time PCR 16S rRNA (AB)+<br>DNA probe 740+<br>DNA probe FlaB+ | |
| (9) blood | Screw cap, 32° C. | Detected in fluid<br>Detected Dieterle stain<br>Bb immuno (MC)+ | Real-time PCR 16S rRNA (AB)+<br>DNA probe 740+ | |
| (9) vaginal 1 | Screw cap, 24 hours at room temperature, then 32° C. | Detected in fluid<br>Detected Dieterle stain<br>Bb immuno (MC)+ | Real-time PCR 16S rRNA (AB) +/−<br>DNA probe FlaB+ | |

TABLE 1-continued

Data Summary Lyme cultures Comparison of Different specimens collected from the same individual using different culture methods

| Sample ID of culture, type of inoculum (scew cap - microaerobic) (patient number) | Transport and Culture conditions (screw cap - microaerophillic, anaerobic jar) | Microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (9) vaginal 2 | Screw cap, 24 hours at room temperature, then 32° C. | Detected in fluid Detected Dieterle stain Bb immuno (MC)+ | Real-time PCR 16S rRNA (AB)+ Endpoint rpoC | rpoC Bbss |
| (10) blood | Screw cap, 32° C. | Detected in fluid Detected Dieterle stain Bb immuno (MC)+ | Real-time PCR 16S rRNA (AB)+ Endpoint rpoC+ DNA probe 740+ | |
| (10) vaginal | Screw cap, 24 hours transported winter with freezing conditions, then 32° C. | Detected in fluid Bb immuno (UNH)+ Bb immuno (MC)+ | | |
| (11) blood | Screw cap, 32° C. | Detected in fluid Bb immuno (UNH)+ Bb immuno (MC)+ | GAPDH+ Real-time PCR 16S rRNA (AB)+ Endpoint rpoC+ | rpoC *Borrelia* spp. Bbss |
| (11) vaginal | Screw cap, 24 hours at room temperature, then 32° C. | Detected in fluid Bb immuno (UNH)+ Bb immuno (MC)+ | Nested Fla+ Real-time PCR 16S rRNA (AB)+ Endpoint rpoC+ DNA probe 740+ DNA probe FlaB+ | Fla Bbss rpoC *B. hermsii* |
| (12) blood | Screw cap, 1 hour transport, then 32° C. | Detected in fluid | Real-time PCR 16S rRNA (AB)+ Endpoint rpoC+ | rpoC *Borrelia* spp. |
| (12) seminal | Screw cap, overnight at room temperature, then 32° C. | Detected in fluid | Real-time PCR 16S rRNA (AB)+ Endpoint rpoC+ | rpoC 2 amplicons 1. Bb ss 2. *B. miyamotoi* |
| (13) blood | Screw cap 32° C. | Detected in fluid Detected Dieterle stain Bb immuno (MC) + | Real-time PCR 16S rRNA (AB) +/− Endpoint rpoC+ | rpoC *Borrelia* spp. |

TABLE 2

Collected, inoculated at room temperature with no special equipment

| Sample ID of culture, type of inoculum (screw cap - microaerobic) | Transport and Culture conditions (screw cap - microaerophillic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (14) blood | Warm room incubated 23-32° C., 1 month, screw cap | Detected in fluid | Real-time PCR 16S rRNA (AB)+ Nested PCR Fla+ | Fla Bbss |
| (14) vaginal culture | Warm room 23-32° C., 1 month, screw cap | Detected in fluid | Real-time PCR 16S rRNA (AB)+ End-point PCR rpoC+ | 2 rpoC amplicons 1. Bbss 2. *B. garinii* |
| (15) vaginal | Screw cap, room temperature 3 weeks | | Real-time PCR 16S rRNA (UNH)+ | |
| (16) vaginal | Screw cap, room temperature 3 weeks | | Real-time PCR 16S rRNA (AB)+ | |

TABLE 3

Samples incubated at 32° C. immediately after inoculation. Anaerobic jar indicates a completely anaerobic environment. Screw cap indicates no special equipment (anaerobic jar, or CO₂ enriched jar, or CO₂ incubator) was used to provide a microaerophilic or anaerobic environment

| Sample ID of culture, type of inoculum (screw cap - microaerobic) | Transport and Culture conditions (screw cap - microaerophillic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (1) blood | 32° C. anaerobic jar | Detected in fluid<br>Detected Dieterle stain<br>Bb immuno (MC)+ | Nested PCR 16S rRNA+<br>Nested PCR Fla+ | 16S rRNA Bbss |
| (17) blood | 32° C. anaerobic | Detected in fluid<br>Detected Dieterle stain<br>Bb immuno (MC)+ | Nested PCR 16S rRNA+<br>Nested PCR Fla+ | |
| (18) blood | 32° C. anaerobic | Detected in fluid<br>Detected Dieterle<br>Bb immuno (MC)+ | Nested PCR Fla+<br>DNA probe 740+ | |
| (19) blood | 32° C. anaerobic | Detected in fluid | Nested PCR Fla+<br>Nested PCR pyrG+ | Fla Bbss |
| (20) skin | 32° C. anaerobic | Detected in fluid | Nested PCR Fla+ | Fla Bbss |
| (21) blood | 32° C. anaerobic | Detected in fluid<br>Detected Dieterle stain<br>Bb immuno (MC)+ | Real-time 16S rRNA (AB)+<br>Nested PCR pyrG+ | |
| (21) skin | 32° C. anaerobic | Detected in fluid<br>Detected Dieterle stain<br>Bb immuno (MC)+ | Nested PCR pyrG+ | |
| (22) blood | 32° C. anaerobic | Detected in fluid | Real-time PCR 16S rRNA (AB)+<br>Nested PCR Fla+ | Fla Bbss |
| (22) vaginal | 32° C. anaerobic | Detected in fluid | Real-time PCR 16S rRNA (AB)+<br>Nested PCR Fla+ | Fla Bbss |
| (23) blood | Screw cap, 32° C. | Detected in fluid<br>Detected Dieterle<br>Bb immuno (MC)+ | Real-time PCR 16S rRNA (UNH)+/− | |
| (24) skin | 32° C., screw cap | Detected in fluid | Real-time PCR 16S rRNA (AB)+/−<br>DNA FlaB probe+ | |
| (24) vaginal | 32° C. screw cap | Detected in fluid | DNA probe 740+ | |
| (2) blood | 32° C. anaerobic | Detected in fluid<br>Detected Dieterle<br>Bb immuno (MC)+ | Nested 16s rRNA+<br>Real-time 16S rRNA (AB)+<br>End point PCR rpoC+ | 16S rRNA BbSS<br>rpoC Bbss |
| (2) semen | Screw cap, 32° C. | Detected in fluid<br>Detected Dieterle<br>Bb immuno (MC)+ | DNA probe 740+<br>Real-time PCR 16S rRNA (UNH)+<br>Nested 16S rRNA+<br>Real-time 16srRNA (AB)+<br>Endpoint rpoC+ | 16S rRNA Bbss<br>rpoC Bbss |
| (2) semen 1 month treatment doxycycline | Screw cap, 32° C. | Detected in fluid<br>Detected Dieterle<br>Bb immuno (MC)+ | | |
| (2) semen 4 months treatment antibiotics | Screw cap, 32° C. | Detected in fluid | Real-time 16srRNA (AB)+<br>Endpoint rpoC+ | rpoC Bbss |
| (2) periodontal | Screw cap, 32° C. | Detected in fluid<br>Detected Dieterle<br>Bb immuno (MC)+ | Real-time 16srRNA (AB)+<br>Endpoint rpoC+ | rpoC *Borrelia* spp. |
| (3) blood | 32° C. anaerobic | Detected in fluid<br>Detected Dieterle stain<br>Bb immuno (MC)+ | Nested PCR pyrG+<br>Nested PCR 16S rRNA+<br>Real-time 16srRNA (AB)+<br>Endpoint rpoC+<br>probe 740+<br>probe FlaB+ | 16S rRNA partial sequence<br>rpoC Bbss |
| (3) vaginal | Screw cap, 32° C. | Detected in fluid<br>Detected Dieterle stain<br>Bb immuno (MC)+ | Real-time PCR 16S rRNA (UNH)+<br>Nested PCR, Fla+,<br>Nested pyrG+,<br>Nested 16SrRNA+<br>Real-time 16srRNA (AB)+<br>Endpoint rpoC+<br>probe 740+<br>probe FlaB+ | rpoC Bbss |
| (3) vaginal 1 month of Omnicef/Biaxin | Screw cap, 32° C. | Detected in fluid<br>Detected Dieterle stain<br>Bb immuno (MC)+ | Real-time 16srRNA (AB)+<br>Endpoint rpoC+ | rpoC Bbss |
| (4) blood | Anaerobic, 32° C. | Detected in fluid<br>SEM | Nested pyrG+<br>Real-time PCR (AB)+ | |
| (4) vaginal | Screw cap, 32° C. | Detected in fluid<br>Bb immuno (UNH)+ | Real-time PCR (UNH)+<br>Real-time 16srRNA (AB)+<br>Endpoint rpoC+<br>probe 740+ | rpoC Bbss |

TABLE 3-continued

Samples incubated at 32° C. immediately after inoculation. Anaerobic jar indicates a completely anaerobic environment. Screw cap indicates no special equipment (anaerobic jar, or CO$_2$ enriched jar, or CO$_2$ incubator) was used to provide a microaerophilic or anaerobic environment

| Sample ID of culture, type of inoculum (screw cap - microaerobic) | Transport and Culture conditions (screw cap - microaerophillic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (25) blood | Screw cap, 32° C. | Detected Dieterle stain<br>Bb immuno (MC)+ | Real-time PCR (UNH)+<br>Nested Fla+<br>Real-time 16srRNA (AB)+/− | Fla Bbss |
| (25) semen | Screw cap, 32° C. | Detected Dieterle stain<br>Bb immuno (MC)+ | Real-time PCR (UNH)+<br>Real-time 16srRNA (AB)+/−<br>FlaB probe+ | |
| (26) blood | Screw cap, 32° C. | Detected Dieterle stain<br>Bb immuno (MC)+ | Nested Fla+<br>Real-time PCR (UNH)+ | Fla Bbss |
| (27) blood | Screw cap, 32° C. | Detected in fluid<br>Detected Dieterle stain<br>Bb immuno (MC)+ | Real-time PCR 16S rRNA (UNH)+<br>Nested Fla+<br>Real-time 16srRNA (AB)+ | Fla Bbss |
| (27) vaginal | Screw cap, 32° C. | Detected Dieterle stain<br>Bb immuno (MC)+ | Real-time PCR 16S rRNA (UNH)+<br>FlaB probe+<br>Real-time 16srRNA (AB)+ | |
| (28) blood | Screw cap, 32° C. | Detected in fluid<br>Detected Dieterle stain<br>Bb immuno (MC)+ | Real-time PCR 16S rRNA (UNH)+<br>Nested FlaB+<br>Real-time 16srRNA (AB)+<br>DNA probe 740+ | |
| (29) Blood | Screw cap 32° C. | Detected in fluid<br>Detected Dieterle stain<br>Bb immuno (MC)+ | Real-time PCR 16S rRNA (UNH)+<br>Nested pyrG<br>Real-time PCR 16S rRNA (AB)+<br>DNA probe 740+ | |
| (8) blood | Screw cap 32° C. | Detected in fluid<br>Detected Dieterle stain<br>Bb immuno (MC)+ | Nested pyrG+<br>Real-time PCR 16S rRNA (AB)+<br>DNA probe 740+ | |
| (9) blood | Screw cap, 32° C. | Detected in fluid<br>Detected Dieterle stain<br>Bb immuno (MC)+ | Real-time PCR 16S rRNA (AB)+<br>DNA probe 740+ | |
| (10) blood | Screw cap, 32° C. | Detected in fluid<br>Detected Dieterle stain<br>Bb immuno (MC)+ | Real-time PCR 16S rRNA (AB)+<br>Endpoint rpoC+<br>DNA probe 740+ | |
| (11) blood | Screw cap, 32° C. | Detected in fluid<br>Bb inimuno (UNH)+<br>Bb immuno (MC)+ | GAPDH+<br>Real-time PCR 16S rRNA (AB)+<br>Endpoint rpoC+ | rpoC *Borrelia* spp.<br>Bbss |
| (13) blood | Screw cap 32° C. | Detected in fluid<br>Detected Dieterle stain<br>Bb immuno (MC) + | Real-time PCR 16S rRNA (AB) +/−<br>Endpoint rpoC+ | rpoC *Borrelia* spp. |

TABLE 4

Transported in less than ideal environment
Data Summary Lyme cultures

| Sample ID of culture, type of inoculum (screw cap - microaerobic) | Transport and Culture conditions (screw cap - microaerobic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (1) vaginal | Transported several days variable temperature, screw cap, 32° C. | Detected in fluid<br>Detected Dieterle<br>Bb immuno (MC)+ |

TABLE 4-continued

Transported in less than ideal environment
Data Summary Lyme cultures

| Sample ID of culture, type of inoculum (screw cap - microaerobic) | Transport and Culture conditions (screw cap - microaerobic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (28) skin culture | Transported 1 hour, screw cap, 32° C. | Detected in fluid | Real-time PCR 16S rRNA (AB)+ | |
| (5) semen | Screw cap, overnight at room temperature 23° C., then 32° C. | Detected Dieterle stain Bb immuno (MC)+ | Nested Fla+ Nested 16S rRNA Real-time PCR 16S rRNA (UNH)+ FlaB probe | 16S rRNA *Borrelia* spp. |
| (6) seminal | Screw cap, overnight at room temperature 23° C., then 32° C. | Detected in fluid Detected Dieterle stain Bb immuno (MC)+ SEM | Real-time PCR 16S rRNA (UNH)+ DNA probe 740+ DNA probe FlaB+ | |
| (6) seminal on antibiotics doxycycline | Screw cap, overnight at room temperature 23° C., then 32° C. | Detected in fluid Detected Dieterle stain Bb immuno (MC)+ | Nested PCR GAPHD+ Real-time 16srRNA (AB)+ | |
| (7) vaginal | Screw cap, 24 hours at room temperature 23° C., then 32° C. | Detected in fluid Detected Dieterle stain Bb immuno (MC)+ | Nested GAPHD Real-time PCR 16S rRNA (AB)+ DNA probe 740+ DNA probe FlaB+ | |
| (7) vaginal on antibiotics doxycycline 1 month | Screw cap, 24 hours at room temperature 23° C., then 32° C. | Detected in fluid Detected Dieterle stain Bb immuno (MC)+ | Nested GAPHD+ Real-time PCR 16S rRNA (AB)+ Endpoint rpoC+ | rpoC Bbss |
| (7) vaginal on antibiotics 9 months amoxicilin | Screw cap, 24 hours at room temperature, then 32° C. | Detected in fluid Detected Dieterle stain Bb immuno (MC)+ | Real-time PCR 16S rRNA (AB)+ | |
| (8) vaginal | Screw cap, 24 hours at room temperature, then 32° C. | Detected in fluid Detected Dieterle stain Bb immuno (MC)+ | Real-time PCR 16S rRNA (UNH)+ Nested pyrG+ Real-time PCR 16S rRNA (AB)+ DNA probe 740+ DNA probe FlaB+ | |
| (29) seminal | Screw cap, 24 hours at room temperature, then 32° C. | Detected in fluid Detected Dieterle stain Bb immuno (MC)+ | Nested Fla+ DNA probe 740+ DNA probe FlaB+ | |
| (9) vaginal 1 | Screw cap, 24 hours at room temperature, then 32° C. | Detected in fluid Detected Dieterle stain Bb immuno (MC)+ | Real-time PCR 16S rRNA (AB) +/− DNA probe FlaB+ | |
| (9) vaginal 2 | Screw cap, 24 hours at room temperature, then 32° C. | Detected in fluid Detected Dieterle stain Bb immuno (MC)+ | Real-time PCR 16S rRNA (AB)+ Endpoint rpoC | rpoC Bbss |
| (10) vaginal | Screw cap, 24 hours transported winter with freezing conditions, then 32° C. | Detected in fluid Bb immuno (UNH)+ Bb immuno (MC)+ | | |
| (15) vaginal | Screw cap, room temperature 3 weeks | | Real-time PCR 16S rRNA (UNH)+ | |
| (16) vaginal | Screw cap, room temperature 3 weeks | | Real-time PCR 16S rRNA (AB)+ | |
| (30) seminal | Screw cap, 24 hours at room temperature, then 32° C. | Detected in fluid Dieterle stain+ Bb immuno (MC)+ | Real-time PCR 16S rRNA (AB)+ Endpoint rpoC+ Nested GAPDH+ DNA probe 740+ DNA probe FlaB+ | rpoC *B. hermsii* |
| (11) vaginal | Screw cap, 24 hours at room temperature, then 32° C. | Detected in fluid Bb immuno (UNH)+ Bb immuno (MC)+ | Nested Fla+ Real-time PCR 16S rRNA (AB)+ Endpoint rpoC+ DNA probe 740+ DNA probe FlaB+ | Fla Bbss rpoC *B. hermsii* |
| (31) vaginal 1 | Screw cap, 3 days transport variable temperatures, then 32° C. | Detected in fluid Detected Dieterle stain Bb immuno (MC)+ | Nested GAPDH+ Real-time PCR 16S rRNA (AB)+ Endpoint rpoC+ DNA probe 740+ DNA probe FlaB+ | rpoC Bbss |
| (31) vaginal 2 | Screw cap, 3 days transport variable temperatures including winter conditions, then 32° C. | Detected in fluid | Real-time PCR 16S rRNA (AB)+ | |

TABLE 4-continued

Transported in less than ideal environment
Data Summary Lyme cultures

| Sample ID of culture, type of inoculum (screw cap - microaerobic) | Transport and Culture conditions (screw cap - microaerobic, anaerobic jar) | microscopic confirmation method, (direct examination of fluid, Dieterle stain, Bb-anti-immuno stain (McClains), Bb-anti-immuno University of New Haven (UNH), SEM) | DNA detection and method (Nested PCR, Real-time PCR, Enpoint PCR, hybridization with DNA probe) target | sequence confirmation, amplicon type, closest BLAST match (*B. burgdorferi* sensu stricto Bbss) |
|---|---|---|---|---|
| (32) seminal | Screw cap, 3 days transport variable temperatures including winter conditions, then 32° C. | Detected in fluid Detected Dieterle stain Bb immuno (MC)+ | Nested GAPDH+ Real-time PCR 16S rRNA (AB)+ Endpoint rpoC+ DNA probe 740+ DNA probe FlaB+ | GAPDH Bb ss rpoC *Borrelia* spp. |
| (33) seminal | Screw cap, 3 days transport variable temperatures including winter conditions, then 32° C. | Detected in fluid Detected Dieterle stain Bb immuno (MC)+ | Real-time PCR 16S rRNA (AB)+ DNA probe 740+ DNA probe FlaB+ | |
| (34) blood | Screw cap, 1 hour transport, then 32° C. | Detected in fluid | Real-time PCR 16S rRNA (AB)+ Endpoint rpoC+ | rpoC *Borrelia* spp. |
| (34) seminal | Screw cap, overnight at room temperature, then 32° C. | Detected in fluid | Real-time PCR 16S rRNA (AB)+ Endpoint rpoC+ | rpoC 2 amplicons 1. Bb ss 2. *B. miyamotoi* |
| (35) seminal | Screw cap, overnight at room temperature, then 32° C. | Detected in fluid Detected Dieterle stain Bb immuno (MC)+ | Real-time PCR 16S rRNA (AB)+ | |
| (36) vaginal 1 | Screw cap, overnight at room temperature, then 32° C. | Detected in fluid | Real-time PCR 16S rRNA (AB)+ | |
| (36) vaginal 2 | Screw cap, overnight at room temperature, then 32° C. | Detected in fluid | Real-time PCR 16S rRNA (AB)+ | |
| (37) seminal | Screw cap, overnight at room temperature, then 32° C. | Detected in fluid | Real-time PCR 16S rRNA (AB) +/− Endpoint rpoC+ | rpoC Bb ss |
| (38) vaginal | Screw cap, overnight at room temperature, then 32° C. | Detected in fluid | Real-time PCR 16S rRNA (AB)+ Endpoint PCR rpoC+ | rpoC Bbss |
| (39) seminal | Screw cap, overnight at room temperature, then 32° C. | Detected in fluid | Real-time PCR 16S rRNA (AB) +/− | |
| (40) vaginal | Screw cap, overnight at room temperature, then 32° C. | Detected in fluid | Real-time PCR 16S rRNA (AB)+ | |

Tables 5A and 5B provide controls. Table 5A provides data summary controls and 5B provides staining controls. Negatives are cultures from 4 healthy patients with negative Lyme serology and asymptomatic. Cultures tested negative on all assays.
AB = Australian Biologics, Sydney Australia, UNH = University of New Haven

| Sample ID of culture, type of inoculum (screw cap - microaerobic) | DNA detection and method (Nested PCR, Real-time PCR, Enpoint PCR, hybridization with DNA probe) target |
|---|---|
| Positive control known *B. burgdorferi* (UNH) B-31 (46) | Nested Fla+; Nested pyrG+; Nested 16S rRNA; Nested GAPD; Real-time PCR 16S rRNA (AB) +; Real-time PCR 16S rRNA (UNH)+; Endpoint rpoC+ |
| (41) seminal | Nested Fla−; Nested pyrG−; Real-time PCR 16S rRNA (AB) −; Real-time PCR 16S rRNA (UNH)− |
| (42) seminal | Nested Fla−; Real-time PCR 16S rRNA (AB) −; Real-time PCR 16S rRNA (UNH)− |
| (43) vaginal | Nested Fla−; Nested pyrG−; Real-time PCR 16S rRNA (AB) −; Real-time PCR 16S rRNA (UNH)− |
| (44) vaginal | Real-time PCR 16S rRNA (AB) −; Real-time PCR 16S rRNA (UNH)− |
| Normal human foreskin | Nested Fla−; Nested pyrG−; Nested GAPD−; Nested 16S rRNA−; Real-time PCR 16S rRNA (UNH)− |
| Normal Skin from callused feet | Nested Fla−; Nested pyrG−; Nested 16S rRNA−; Real-time PCR 16S rRNA (AB) −; Real-time PCR 16S rRNA (UNH)− |
| Water | Nested Fla−; Nested pyrG−; Nested GAPD−; Nested 16S rRNA−; Real-time PCR 16S rRNA (AB) −; Real-time PCR 16S rRNA (UNH)− |

Table 5B

| Sample ID of culture, type of inoculum | method, (Dieterle stain, Bb-anti-immuno stain (McClains), Bb-anti-immuno University of New Haven (UNH) | Result |
|---|---|---|
| Mixed gram positive bacteria | anti Bb immuno McClains | negative, no staining |
| Mixed gram negative bacteria | anti Bb immuno McClains | Minimal staining, pale pink |
| Positive control mouse liver section from mouse infected with Bb | anti Bb immuno McClains | Hepatocytes counterstained blue with Hemotoxylin and immuno stained cherry-red spirochetes |
| Negative control mouse liver section from uninfected mouse | anti Bb immuno McClains | Hepatocytes counterstained blue with Hemotoxylin |
| Normal human skin with normal skin flora | anti Bb immuno McClains | Skin cells counterstained blue with Hemotoxylin, bacteria unstained |
| Human skin, psoriasis | anti Bb immuno McClains | Skin cells counterstained blue with Hemotoxylin |
| Human skin, fungal infection | anti Bb immuno McClains | Skin cells counterstained blue with Hemotoxylin |
| Positive control Bb B-31 | anti Bb immuno UNH | Positive, fluorescence |
| *Treponema denticola* | anti Bb immuno UNH | Negative, no staining |
| replacing anti-Bb antibody with normal rabbit serum | anti Bb immuno UNH | Negative, no staining |

TABLE 6

Samples from patients were shipped under uncontrolled conditions by a commercial carrier from Canada to Australia, Finland, California and Connecticut for PCR testing, and all were stable. Patients correspond to those found in Tables 1-5, as indicated.

| Patient ID | Age | Sex | Lyme Serology Laboratory and result |
|---|---|---|---|
| (1) | 56 | female | IGeneX positive |
| (17) | 75 | female | IGeneX positive |
| (27) | 41 | male | IGeneX positive |
| (18) | 51 | female | IGeneX positive |
| (19) | 53 | female | IGeneX negative, diagnosis clinical |
| (20) | 35 | female | Never tested, diagnosis self identified |
| (45) | 63 | female | IGeneX IgG positive |
| (21) | 43 | female | IGeneX positive |
| (22) | 53 | female | IgG positive |
| (23) | 62 | female | IGeneX positive |
| (24) | 37 | female | IGeneX positive |
| (14) | 73 | female | Never tested |
| (28) | — | female | Never tested |
| (2) | 64 | male | IGeneX positive |
| (3) | 54 | female | IGeneX positive |
| (4) | 57 | female | IGeneX indeterminate |
| (25) | 46 | male | IGeneX positive |
| (5) | 36 | male | IGeneX positive |
| (26) | 67 | female | IGeneX positive |
| (6) | 42 | male | IGeneX negative, but IGenex PCR positive whole blood |
| (7) | 41 | female | IGeneX positive |
| (8) | 28 | female | IGeneX positive |
| (29) | 51 | male | IGeneX positive |
| (9) | 34 | female | IGeneX positive |
| (10) | 46 | female | IGeneX negative, clinical diagnosis |
| (16) | 40 | female | IGeneX positive |
| (15) | 45 | female | IGeneX positive |
| (30) | 57 | male | IGeneX positive |
| (11) | 55 | female | IGeneX negative, diagnosis clinical |
| (31) | 54 | female | IGeneX positive |
| (32) | 66 | male | IGeneX positive |
| (33) | 69 | male | IGeneX positive |
| (34) | 55 | male | IGeneX negative, diagnosis clinical |
| (13) | 39 | female | IGeneX positive |
| (35) | 27 | male | IGeneX positive |
| (36) | 43 | female | IGeneX positive |
| (37) | 43 | male | IGeneX positive |
| (38) | 58 | female | IGeneX positive |
| (39) | — | male | IGeneX positive |
| (40) | 42 | female | IGeneX positive |
| Negative controls | | | |
| (41) | 64 | male | IGeneX negative |
| (42) | 54 | male | IGeneX negative |
| (43) | 59 | female | IGeneX negative |
| (44) | 44 | female | IGeneX negative |

Example 2—Direct Detection of Spirochetes from Fresh Blood and Tissue Samples: A Novel Screening Approach for Spirochete Detection Spirochetes were detected directly from fresh blood samples. Samples were obtained using the following protocol.

1. Take blood sample:
   a. venous blood: collect sample of blood in a test tube, using standard recommended phlebotomy procedures, preferably use a tube designed for blood collection (i.e. VACUTAINER®), with or without an anticoagulant such as EDTA, heparin, or sodium citrate. If an anticoagulant is used then centrifuge and select specimen from cells taken from the buffy coat layer, including some red blood cells (RBCs). If a tube without anticoagulant is used, allow blood to clot, 15 to 20 minutes, then centrifuge and take the specimen from the layer between the RBCs and serum, being sure to collect some RBCs as well as clear fluid.
 b. finger prick: clean and disinfect finger, prick finger so that a drop of blood appears on the tip of the finger.
2. Place blood sample on pre-cleaned glass slide.
3. Add a drop of BSK-H medium. This step is optional if blood sample was collected from a tube of blood. This step is recommended if the blood has been taken from a finger prick.
4. Place a clean glass coverslip over the blood sample.
5. Seal edges of the coverslip with a film-forming lacquer, such as nail polish, e.g., a clear nail polish composition comprising a nitrocellulose polymer dissolved in a volatile organic acid such as butyl acetate or ethyl acetate.
6. After edges are sealed with hardened lacquer examine the specimen under 400× or 1000× magnification with a darkfield or brightfield microscope, preferably a darkfield microscope. If present in blood, spirochetes will begin to emerge from the cells shortly after slide preparation. This process first appears around the periphery of the specimen. Spirochetes may be visible very quickly e.g., 15 minutes after slide preparation, but some samples may require longer incubation. In some cases spirochetes can be best seen the day after slide preparation.

Figure 1B:
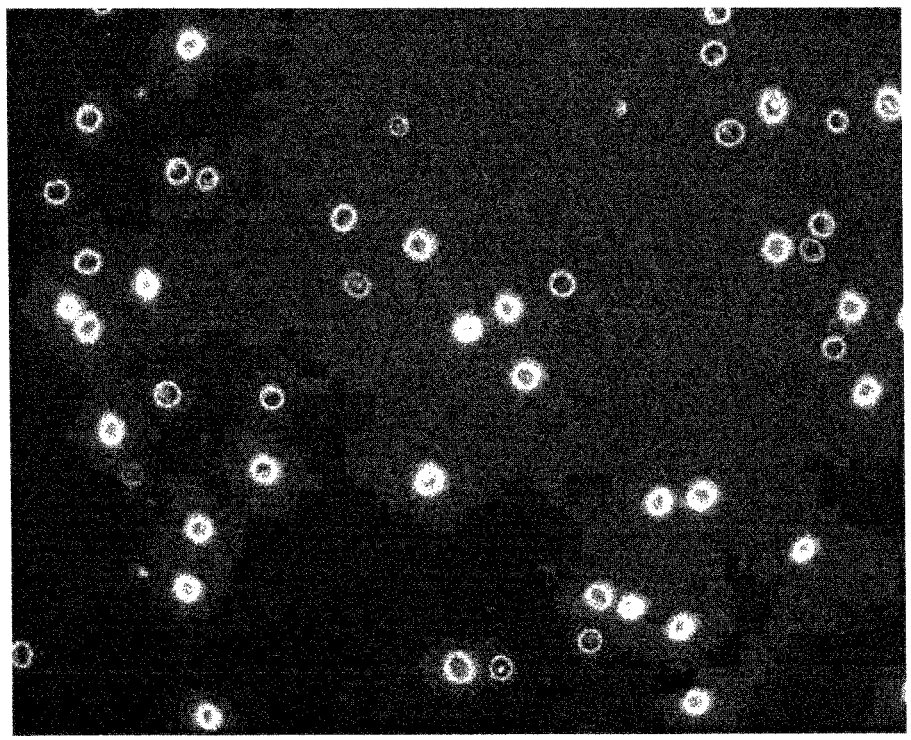
Figure 2A:
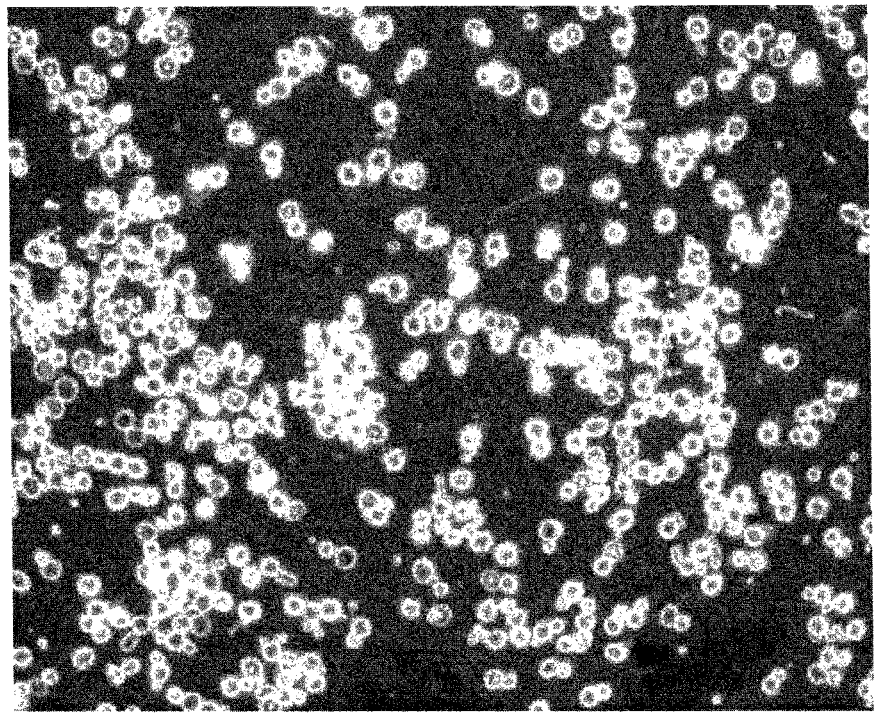
FIGS. 2A and 2B are a photomicrographs of blood samples prepared according to Example 2, using thick blood smears (see below).
Figure 2B:
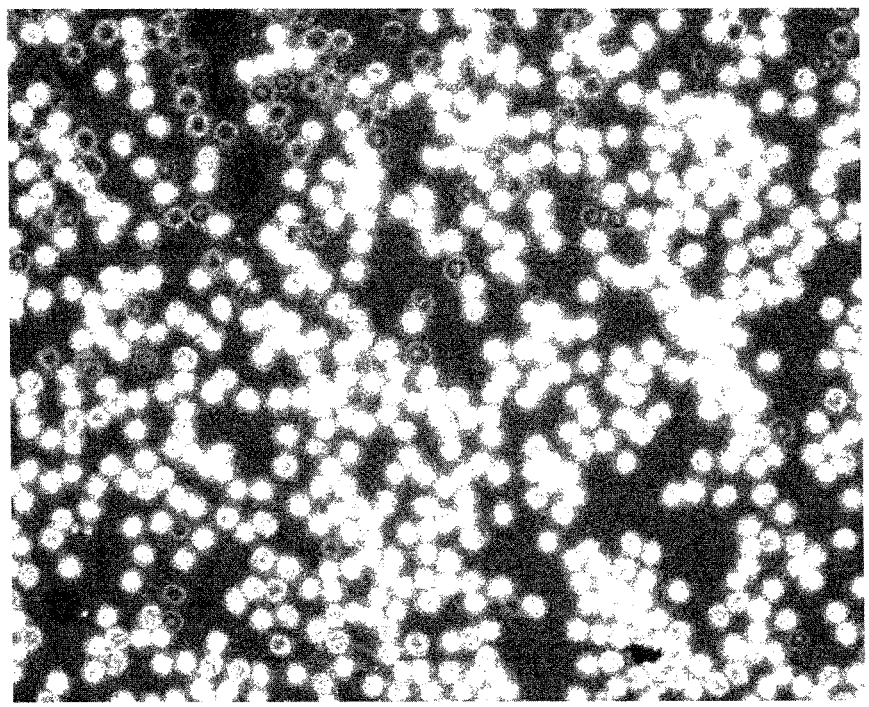

Using this method, blood obtained from a Lyme disease-positive individual was observed, and compared to samples that were prepared in the same manner, but without the film-forming lacquer sealant. Thin blood films (FIGS. 1A and 1B) were tested, with spirochete organisms visible in the sealant-treated specimen, but not in the no-sealant control. Thick blood films (FIGS. 2A and 2B) were tested, with spirochete organisms visible in the sealant-treated specimen, but not in the no-sealant control.

In further testing, blood obtained from six suspected Lyme disease candidates was tested, as well as blood from three negative controls. All samples were sealed as above with the film-forming lacquer sealant. Spirochetes were visualized in blood obtained from all of the suspected Lyme disease candidates, while none were seen in the blood from negative controls.

Figure 3:
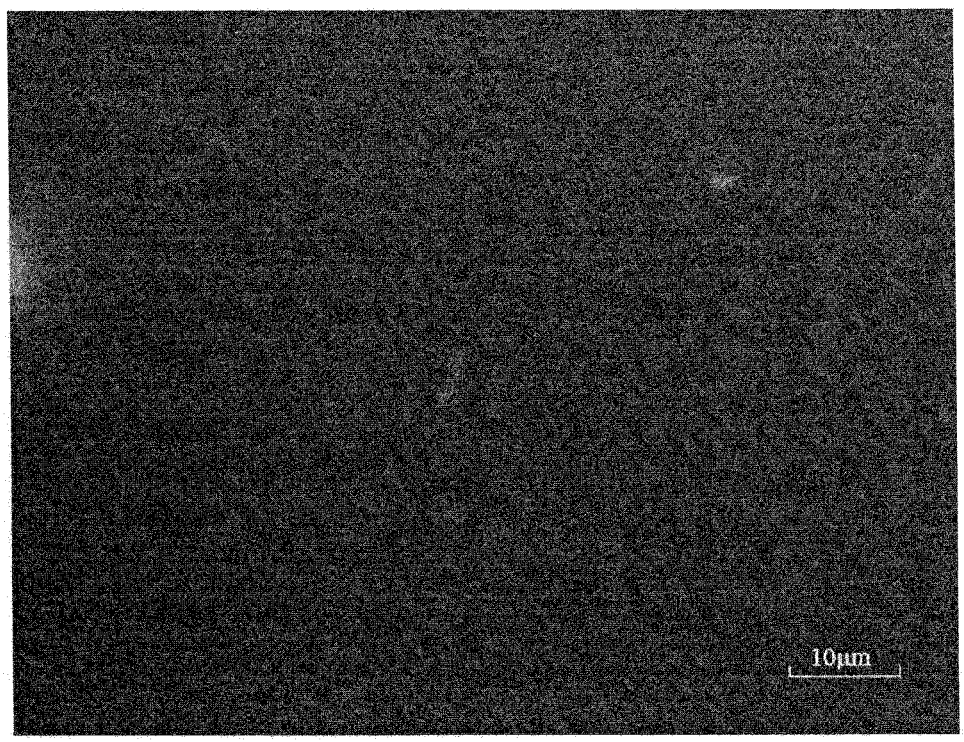
FIG. 3 is a photomicrograph of a skin sample prepared according to Example 2 (see below).

In further testing, a skin culture sample from a Lyme patient was placed on a slide, which was treated and sealed as indicated above. Specifically, a drop of BSK-H was placed on a slide. Skin was obtained by scraping the skin off with a scalpel, then was used to inoculate the BSK-H complete. A cover slip was added. Then the slide was sealed with the film-forming lacquer sealant and incubated overnight. As with the blood samples, above, motile spirochetes were observed (FIG. 3).

The following clauses provide an outline of certain aspects of the present invention:
1. A method of culturing *Borrelia* spirochetes, such as a *B. burgdorferi* spirochete, from a non-sterile specimen, comprising:
 a. inoculating spirochete-supportive complete media in a culture vessel with a sample containing, or which is being tested to contain, *Borrelia* spirochetes, where the medium in combination with the sample fills a sufficient percentage of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes;
 b. sealing the culture vessel with an airtight cap or plug;
 c. storing and/or shipping the culture vessel for a time period of at least 8, 12, 24, 30, 36, 42, or 48 hours in uncontrolled environmental conditions, where at least temperature of the culture vessel is not controlled; and
 d. culturing the sample in the culture vessel in a controlled environment suitable for culture of *Borrelia* spirochetes, thereby expanding a population of *Borrelia* spirochetes present in, or if present in, the sample.
2. A method of obtaining and growing a culturing *Borrelia* spirochetes, such as a *B. burgdorferi* spirochete, from a non-sterile specimen, comprising
 a. receiving from a person a culture vessel comprising a non-sterile biological sample containing, or to be tested for the presence of, *Borrelia* spirochetes, the culture vessel comprising a spirochete-supportive complete medium, where the medium in combination with the sample fills a sufficient percentage of the volume capacity of the culture vessel to produce a microaerobic environment, the spirochete-supportive complete media comprising spirochete-supportive media, antimicrobially-effective amounts of a broad-spectrum antibiotic and a bactericidal antibiotic drug, antifungally-effective amounts of an antifungal agent, and serum in amounts effective to support specific growth of *Borrelia* spirochetes, wherein the culture vessel has been stored and/or shipped for a time period of at least 8, 12, 24, 30, 36, 42, or 48 hours in uncontrolled environmental conditions where at least temperature of the culture vessel is not controlled;
 b. culturing the sample in the culture vessel in a controlled environment suitable for culture of *Borrelia* spirochetes, thereby expanding a population of *Borrelia* spirochetes present in, or if present in, the sample; and
 c. determining if *Borrelia* spirochetes, such as *B. burgdorferi* has grown in the culture medium by looking for the presence of spirochetes, using microscopy methods, PCR and/or real time PCR, or any suitable equivalent genetic testing for the presence of *Borrelia* spirochete, such as *B. burgdorferi* specific genes, and/or immunofluorescence or immunostaining assays that look for *Borrelia* spirochete, such as *B. burgdorferi* specific proteins.
3. The method of clause 2, further comprising prior to receiving step a., shipping to the person a kit for obtaining a sample that contains or is to be tested to contain *Borrelia* spirochetes, the kit comprising:
 i. sterile spirochete-supportive complete media in a culture vessel, where the medium in combination with a sample fills a sufficient percentage of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes;
 ii. a pipet, a sterile swab, a sterile disposable scalpel, a disinfecting swab and a sterile sample collection vessel;
 iii. a return shipping package adapted to receive the culture vessel; and iv. optionally indicia including instructions indicating how to properly store the kit and also how to collect a specimen for inoculation of the media.
4. The method of any one of clauses 1-3, wherein the spirochete-supportive media is selected from the group consisting of BSK-H, BSK-II and MKP.
5. The method of any one of clauses 1-3, wherein the spirochete-supportive media is BSK-H.

6. The method of any one of clauses 1-3, wherein the broad-spectrum antibiotic is selected from the group consisting of ampicillin, streptomycin, levofloxacin, gatifloxacin, moxifloxacin, ciprofloxacin, and phosphomycin.
7. The method of any one of clauses 1-3, wherein the broad-spectrum antibiotic is phosphomycin.
8. The method of any one of clauses 1-7, wherein the broad-spectrum antibiotic is present in the spirochete-supportive complete media at a concentration between 0.01 mg/ml-0.03 mg/ml.
9. The method of any one of clauses 1-3, wherein the bactericidal antibiotic drug is selected from the group consisting of rifabutin, rifapentine, rifaximin, and rifampicin
10. The method of any one of clauses 1-3, wherein the bactericidal antibiotic drug is rifampicin.
11. The method of any one of clauses 1-10, wherein the bactericidal antibiotic drug is present in the spirochete-supportive complete media at a concentration between 0.04 mg/ml-0.06 mg/ml.
12. The method of any one of clauses 1-3, wherein the antifungal is selected from the group consisting of amphotericin B, candicidin, filipin, hamycin, natamycin, nystatin, and rimocidin, fluconazole, itraconazole, miconazole, and terbinafine.
13. The method of any one of clauses 1-3, wherein the antifungal is amphotericin B.
14. The method of any one of clauses 1-13, wherein the antifungal agent is present in the spirochete-supportive complete media at a concentration between 0.0010 mg/ml-0.0040 mg/ml.
15. The method of any one of clauses 1-3, wherein the suitable cell culture serum is selected from the group consisting of fetal bovine serum, fetal calf serum, horse serum, rabbit serum, chicken serum, caprine (goat) serum, human serum, ovine (sheep) serum, and porcine (pig) serum.
16. The method of any one of clauses 1-3, wherein the cell culture serum is rabbit serum.
17. The method of any one of clauses 1-3, wherein the concentration of cell culture serum is between 5% and 10%.
18. The method of any one of clauses 1-17, in which the medium in combination with a sample fills 95% to 100% of the volume capacity of the culture vessel.
19. The method of any one of clauses 1-17, in which the medium in combination with a sample fills 99% to 100% of the volume capacity of the culture vessel.
20. The method of any one of clauses 1-19, in which the sample is semen and the kit comprises a sterile sample vessel for collecting the semen and a pipet for dispensing semen into the culture vessel.
21. The method of any one of clauses 1-19, in which the sample is vaginal, oral or wound and the kit comprises a swab and scalpel.
22. The method of any of clauses 1-21 in which the *Borrelia* spirochete is a *B. burgdorferi* spirochete.
23. A kit for obtaining a sample that contains or is to be tested to contain *Borrelia* spirochetes, such as a *B. burgdorferi* spirochete, the kit comprising:
   a. sterile spirochete-supportive complete media in a culture vessel, where the medium in combination with a sample fills a sufficient percentage of the volume capacity of the culture vessel to produce a microaerobic environment, the spirochete-supportive complete media comprising spirochete-supportive media, a broad-spectrum antibiotic, a bactericidal antibiotic drug, an antifungal agent and serum in amounts effective to support specific growth of *Borrelia* spirochetes;
   b. a pipet, a sterile swab, a sterile disposable scalpel, a disinfecting swab and a sterile sample collection vessel;
   c. a return shipping package adapted to receive the culture vessel; and
   d. optionally indicia including instructions indicating how to store the kit and how to collect a specimen for inoculation of the media.
24. The kit of clause 23, wherein the spirochete-supportive media is selected from the group consisting of BSK-H, BSK-II and MKP.
25. The kit of clause 23, wherein the spirochete-supportive media is BSK-H.
26. The kit of clause 23, wherein the broad-spectrum antibiotic is selected from the group consisting of ampicillin, streptomycin, levofloxacin, gatifloxacin, moxifloxacin, ciprofloxacin, and phosphomycin.
27. The kit of clause 23, wherein the broad-spectrum antibiotic is phosphomycin.
28. The kit of clause 27, wherein the broad-spectrum antibiotic is present in the spirochete-supportive complete media is at a concentration between 0.01 mg/ml-0.03 mg/ml.
29. The kit of clause 23, wherein the bactericidal antibiotic drug is selected from the group consisting of rifabutin, rifapentine, rifaximin, and rifampicin
30. The kit of clause 23, wherein the bactericidal antibiotic drug is rifampicin.
31. The kit of clause 30, wherein the bactericidal antibiotic drug is present in the spirochete-supportive complete media is at a concentration between 0.04-0.06 mg/ml.
32. The kit of clause 23, wherein the antifungal is selected from the group consisting of amphotericin B, candicidin, filipin, hamycin, natamycin, nystatin, and rimocidin.
33. The kit of clause 23, wherein the antifungal is amphotericin B.
34. The kit of clause 23, wherein the antifungal agent is present in the spirochete-supportive complete media is at a concentration between 0.0010 mg/ml-0.0040 mg/ml.
35. The kit of clause 23, wherein the suitable cell culture serum is selected from the group consisting of fetal bovine serum, fetal calf serum, horse serum, rabbit serum, chicken serum, caprine (goat) serum, human serum, ovine (sheep) serum, and porcine (pig) serum.
36. The kit of clause 23, wherein the cell culture serum is rabbit serum.
37. The kit of clause 23, wherein the concentration of cell culture serum is between 5% and 10%.
38. The kit of any one of clauses 23-37, in which the medium in combination with a sample fills 95% to 100% of the volume capacity of the culture vessel.
39. The kit of any one of clauses 23-37, in which the medium in combination with a sample fills 99% to 100% of the volume capacity of the culture vessel.
40. The kit of any one of clauses 23-37, in which the sample is semen and the kit comprises a sterile sample vessel for collecting the semen and a pipet for dispensing semen into the culture vessel.
41. The kit of any one of clauses 23-37, in which the sample is vaginal, oral or wound and the kit comprises a swab.
42. Use of the kit of any one of clauses 23-41, in which a non-sterile specimen, needed for testing the presence of *Borrelia* spirochetes, is obtained and cultured, comprising:
   e. receiving from a person a culture vessel comprising a non-sterile biological sample containing, or to be tested for the presence of, *Borrelia* spirochetes, the culture vessel comprising a spirochete-supportive complete medium, where the medium in combination with the sample fills a sufficient percentage of the volume capacity of the culture vessel to produce a microaerobic environment, the spirochete-supportive complete media comprising spirochete-supportive media, antimicrobially-effective amounts of a broad-spectrum antibiotic and a bactericidal antibiotic drug, antifungally-effective amounts of an antifungal agent, and serum in amounts effective to support specific growth of *Borrelia* spirochetes, wherein the culture vessel has been stored and/or shipped for a time period of at least 8, 12, 24, 30, 36, 42, or 48 hours in uncontrolled environmental conditions where at least temperature of the culture vessel is not controlled;

f. culturing the sample in the culture vessel in a controlled environment suitable for culture of *Borrelia* spirochetes, thereby expanding a population of *Borrelia* spirochetes present in, or if present in, the sample; and g. determining if *Borrelia* spirochetes have grown in the culture medium by looking for the presence of spirochetes, using microscopy methods, PCR and/or real time PCR, or any suitable equivalent genetic testing for the presence of *Borrelia* spirochete, such as *B. burgdorferi* specific genes, and/or immunofluorescence or immunostaining assays that look for *Borrelia* spirochete, such as *B. burgdorferi* specific proteins.

43. A method of diagnosing Lyme disease in a patient, comprising detecting the presence of *Borrelia burgdorferi* in the patient from a semen, vaginal, periodontal or skin sample according to a method of one or clauses 1-22.

44. A method of identifying the presence of a spirochete in a specimen, comprising:
    a. placing the specimen comprising cells on a microscope slide, where the specimen is either suspected of containing a spirochete, or contains a spirochete;
    b. placing a cover slip on the biological specimen on the microscope slide; and
    c. sealing edges of the cover slip, or otherwise contacting the specimen with a polymer in an organic solvent.

45. The method of clause 44, in which the specimen is blood or tissue, the polymer in an organic solvent is a film-forming lacquer, such as nail polish or a composition comprising nitrocellulose in an organic solvent, such as an acetate solvent, such as ethyl acetate, butyl acetate or a $C_{1-6}$ alkyl acetate.

We claim:

1. A method of obtaining and growing a *Borrelia* spirochetes, such as a *B. burgdorferi* spirochete, from a non-sterile specimen, comprising
   a. receiving from a person a culture vessel comprising a non-sterile biological sample containing, or to be tested for the presence of, *Borrelia* spirochetes, the culture vessel comprising a spirochete-supportive complete medium, where the medium in combination with the sample fills a sufficient percentage of the volume capacity of the culture vessel to produce a microaerobic environment, the spirochete-supportive complete medium comprising spirochete-supportive medium, antimicrobially-effective amounts of a broad-spectrum antibiotic and a bactericidal antibiotic drug, antifungally-effective amounts of an antifungal agent, and serum in amounts effective to support specific growth of *Borrelia* spirochetes, wherein the culture vessel has been stored and/or shipped for a time period of at least 8 hours in uncontrolled environmental conditions where at least temperature of the culture vessel is not controlled;
   b. culturing the sample in the culture vessel in a controlled environment suitable for culture of *Borrelia* spirochetes, thereby expanding a population of *Borrelia* spirochetes present in, or if present in, the sample; and
   c. determining if *Borrelia* spirochetes, such as *B. burgdorferi* have grown in the spirochete-supportive complete medium by looking for the presence of spirochetes, using microscopy methods, PCR and/or real time PCR, or any suitable equivalent genetic testing for the presence of *Borrelia* spirochete, such as *B. burgdorferi* specific genes, and/or immunofluorescence or immunostaining assays that look for *Borrelia* spirochete, such as *B. burgdorferi* specific proteins.

2. The method of claim 1, further comprising prior to receiving step a., shipping to the person a kit for obtaining a sample that contains or is to be tested to contain *Borrelia* spirochetes, the kit comprising:
   i. sterile spirochete-supportive complete medium in a culture vessel, where the spirochete-supportive complete medium in combination with a sample fills a sufficient percentage of the volume capacity of the culture vessel to produce a microaerobic environment, the spirochete-supportive complete medium comprising spirochete-supportive media, a broad-spectrum antibiotic, a bactericidal antibiotic drug, an antifungal agent and serum in amounts effective to support specific growth of *Borrelia* spirochetes;
   ii. a pipet, a sterile swab, a sterile disposable scalpel, a disinfecting swab and a sterile sample collection vessel;
   iii. a return shipping package adapted to receive the culture vessel; and
   iv. optionally, indicia including instructions indicating how to properly store the kit and also how to collect a specimen for inoculation of the spirochete-supportive complete medium.

3. The method of claim 1, wherein the spirochete-supportive medium is selected from the group consisting of BSK-H, BSK-II and MKP.

4. The method of claim 1, wherein the broad-spectrum antibiotic is selected from the group consisting of ampicillin, streptomycin, levofloxacin, gatifloxacin, moxifloxacin, ciprofloxacin, and phosphomycin.

5. The method of claim 1, wherein the bactericidal antibiotic drug is selected from the group consisting of rifabutin, rifapentine, rifaximin, and rifampicin.

6. The method of claim 1, wherein the antifungal is selected from the group consisting of amphotericin B, candicidin, filipin, hamycin, natamycin, nystatin, and rimocidin, fluconazole, itraconazole, miconazole, and terbinafine.

7. The method of claim 1, wherein the serum is selected from the group consisting of fetal bovine serum, fetal calf serum, horse serum, rabbit serum, chicken serum, caprine (goat) serum, human serum, ovine (sheep) serum, and porcine (pig) serum.

8. The method of claim 1, wherein the concentration of the serum is between 5% and 10%.

9. The method of claim 1, in which the spirochete-supportive complete medium in combination with a sample fills 95% to 100% of the volume capacity of the culture vessel.

10. The method of claim 2, in which the sample is semen and the kit comprises a sterile sample vessel for collecting the semen and a pipet for dispensing semen into the culture vessel.

11. The method of claim 2, in which the sample is vaginal, oral, or wound and the kit comprises a swab and scalpel.

12. A kit for obtaining a sample that is to be tested to determine if said sample contains *Borrelia* spirochetes, such as a *B. burgdorferi* spirochete, the kit comprising:
   a. sterile spirochete-supportive complete medium in a culture vessel, where the spirochete-supportive complete medium in combination with a sample fills a sufficient percentage of the volume capacity of the culture vessel to produce a microaerobic environment, the spirochete-supportive complete medium comprising spirochete-supportive media, a broad-spectrum antibiotic, a bactericidal antibiotic drug, an antifungal agent and serum in amounts effective to support specific growth of *Borrelia* spirochetes;
   b. a pipet, a sterile swab, a sterile disposable scalpel, a disinfecting swab and a sterile sample collection vessel;
   c. a return shipping package adapted to receive the culture vessel; and
   d. optionally indicia including instructions indicating how to store the kit and how to collect a specimen for inoculation of the spirochete-supportive complete medium.

13. The kit of claim 12, wherein the spirochete-supportive medium is selected from the group consisting of BSK-H, BSK-II and MKP.

14. The kit of claim 12, wherein the broad-spectrum antibiotic is selected from the group consisting of ampicillin, streptomycin, levofloxacin, gatifloxacin, moxifloxacin, ciprofloxacin, and phosphomycin.

15. The kit of claim 12, wherein the bactericidal antibiotic drug is selected from the group consisting of rifabutin, rifapentine, rifaximin, and rifampicin.

16. The kit of claim 12, wherein the antifungal is selected from the group consisting of amphotericin B, candicidin, filipin, hamycin, natamycin, nystatin, and rimocidin.

17. The kit of claim 12, wherein the serum is selected from the group consisting of fetal bovine serum, fetal calf serum, horse serum, rabbit serum, chicken serum, caprine (goat) serum, human serum, ovine (sheep) serum, and porcine (pig) serum.

18. The kit of claim 12, in which the spirochete-supportive complete medium in combination with a sample fills 95% to 100% of the volume capacity of the culture vessel.

19. A method of diagnosing Lyme disease in a patient, comprising detecting the presence of *Borrelia burgdorferi* in the patient from a semen, vaginal, periodontal, or skin sample according to the method of claim 1.

* * * * *

UNITED STATES PATENT AND TRADEMARK OFFICE
CERTIFICATE OF CORRECTION

PATENT NO.         : 10,613,084 B2
APPLICATION NO.    : 15/539442
DATED              : April 7, 2020
INVENTOR(S)        : Marianne Middelveen et al.

Page 1 of 1

It is certified that error appears in the above-identified patent and that said Letters Patent is hereby corrected as shown below:

On the Title Page

Column 2, Line 9, in Other Publications, delete "burgadorferi" and insert -- burgdorferi --

Column 2, Line 13, in Other Publications, delete "senso" and insert -- sensu --

Signed and Sealed this
Twenty-fifth Day of August, 2020

Andrei Iancu
*Director of the United States Patent and Trademark Office*